US010522337B2

United States Patent
Rizzo et al.

(10) Patent No.: US 10,522,337 B2
(45) Date of Patent: Dec. 31, 2019

(54) HIGH-THROUGHPUT CRYOGENIC SPECTROSCOPY FOR GLYCAN ANALYSIS

(71) Applicant: ECOLE POLYTECHNIQUE FEDERALE DE LAUSANNE (EPFL), Lausanne (CH)

(72) Inventors: Thomas Rizzo, Denens (CH); Stephan Warnke, Yverdon (CH); Ahmed Ben Faleh, Renens (CH); Valeriu Scutelnic, Ecublens VD (CH)

(73) Assignee: ECOLE POLYTECHNIQUE FEDERALE DE LAUSANNE (EFPL), Lausanne (CH)

( * ) Notice: Subject to any disclaimer, the term of this patent is extended or adjusted under 35 U.S.C. 154(b) by 0 days.

(21) Appl. No.: 16/212,875

(22) Filed: Dec. 7, 2018

(65) Prior Publication Data
US 2019/0180997 A1    Jun. 13, 2019

Related U.S. Application Data

(60) Provisional application No. 62/596,162, filed on Dec. 8, 2017.

(51) Int. Cl.
*H01J 49/04*    (2006.01)
*H01J 49/00*    (2006.01)
(Continued)

(52) U.S. Cl.
CPC ............ *H01J 49/0481* (2013.01); *G01N 1/28* (2013.01); *G01N 21/3504* (2013.01);
(Continued)

(58) Field of Classification Search
USPC ........................................ 250/287, 281, 282
See application file for complete search history.

(56) References Cited

U.S. PATENT DOCUMENTS

| 8,835,839 B1 | 9/2014 | Anderson et al. |
| 2015/0168318 A1* | 6/2015 | Beckman ............ H01J 49/0431 250/307 |

(Continued)

FOREIGN PATENT DOCUMENTS

WO    WO 2016/069104    5/2016

*Primary Examiner* — Kiet T Nguyen
(74) *Attorney, Agent, or Firm* — Sheridan Ross P.C.

(57) ABSTRACT

A method for analyzing a plurality of molecules with cryogenic vibrational spectroscopy including the steps of providing a packet of molecules in a ionized form, injecting the packet into an ion mobility section, spatially separating the ions of the packet into subpackets according to their collisional cross section (CCS), recompressing the subpackets, by removing an empty space between them, loading the ions into a cryogenic ion trap by keeping subpackets with different collisional cross section in a respective separate compartment, cooling the ions in collisions with a buffer gas, tagging the ions by attaching a messenger molecule, sending a pulse to the trap to excite vibrations of the cold, trapped, and messenger-tagged ions, and separately ejecting ion subpacket from the trap into an extraction region of a time-of-flight mass spectrometer and measuring the number of remaining messenger-tagged ions and untagged ions for each subpacket.

14 Claims, 12 Drawing Sheets

(51) Int. Cl.
*H01J 49/40* (2006.01)
*G01N 1/28* (2006.01)
*G01N 27/62* (2006.01)
*G01N 21/3504* (2014.01)

(52) U.S. Cl.
CPC ........ *G01N 27/622* (2013.01); *H01J 49/0031* (2013.01); *H01J 49/403* (2013.01); *G01N 2201/06113* (2013.01)

(56) References Cited

U.S. PATENT DOCUMENTS

2016/0071715 A1   3/2016  Anderson et al.
2019/0204272 A1*  7/2019  Rizzo .................. G01N 27/622

* cited by examiner ion packets in separate
compartments of an ion trap

HIGH-THROUGHPUT CRYOGENIC SPECTROSCOPY FOR GLYCAN ANALYSIS

CROSS-REFERENCE TO RELATED APPLICATIONS

The present application claims priority to the United States provisional patent application with the Ser. No. 62/596,162 that was filed on Dec. 8, 2017, the contents thereof being herewith incorporated by reference in its entirety.

FIELD OF THE INVENTION

The invention relates to a method, device, and system for molecular analysis, more particular glycan analysis.

BACKGROUND DISCUSSION

State of the Art and Objectives

Motivation—the Importance of Glycan Analysis

The central tenet of molecular biology is that information encoded in DNA is transcribed into RNA, which in turn is translated into proteins—the molecules responsible for much of the functioning of living systems. The precise template-based nature of this information transfer allows one to use information from one class of biological molecules to learn about, and manipulate, another [1]. This tight connection was the driving force behind the Human Genome Project, which has been responsible for a revolution in the study of biology and medicine.

The picture isn't as neat and tidy as it may seem, however. Many, if not most, proteins are modified after their translation from RNA. One of most common post-translations modifications is the attachment of another class of biopolymer, glycans (otherwise known as carbohydrates, oligosaccharides or sugars), to the side-chains of certain amino-acid residues in proteins. This process, known as glycosylation, can modify the function, activity, or localization of a protein and hence plays a key role in living systems. Glycans attached to proteins or lipids are present at the surface of almost all cells and mediate cell-to-cell recognition and signaling, for example [2-5]. They largely govern the interaction of cells with bacteria and viruses and are central to immune response and inflammation [6]. Glycan molecules on the surface red blood cells define the various blood groups. In one way or another, glycans are implicated in virtually all major human diseases [1, 2, 4, 5]. Understanding these fundamental biological processes requires knowing the structure of the glycan molecules involved.

In addition to these fundamental motivations for analyzing glycan structure, there are also practical reasons. Biotherapeutics, or biologics, are drugs cultivated in living cells and used to treat a wide variety of diseases such as cancer, inflammatory and autoimmune diseases, and rare genetic disorders. Approximately half the drugs currently in the pharmaceutical pipeline are biologics, and they represent the fastest growing segment of the therapeutic drug market. These biological drugs can be produced in different types of cells and under different conditions, which leads to differences in the glycosylation pattern, which in turn can affect the drug's effectiveness and cytotoxicity [7-13]. Analysis of the glycans attached to these protein therapeutics is thus an important part of the approval process by regulatory bodies [13-15].

There are two factors that render the structural analysis of glycans particularly complex, however. One is that unlike proteins, glycan biosynthesis is not template-driven—one cannot determine the sequence by reading a code embedded in DNA. It is controlled by the enzymes that link individual monosaccharide building blocks together and trim them, and it is influenced by the cellular environment in which a glycan is produced. One must therefore analyze the glycans themselves to determine their structure.

The other complicating factor comes from the intrinsic chemical nature of glycans—in particular, the wide variety of possible isomerisms:

(1) Unlike linear sequences of monomers with distinct mass as found in proteins and DNA, many of the monosaccharide building blocks of glycans are isomeric, differing only in the stereochemistry of the asymmetric carbon atoms.

(2) The glycosidic bond linking monosaccharides involves a stereogenic carbon, leading to isomeric $\alpha$ and $\beta$ anomers.

(3) Glycosidic bonds can have different attachment points, leading to different regioisomers.

(4) A single monosaccharide unit can support multiple glycosidic bonds, leading to the formation of branched structures that are isomeric with the corresponding linear chains of the same monosaccharide content.

(5) The large number of OH groups allow glycans to be functionalized at different locations, producing a variety of positional isomers.

Because these various types of isomerism are present simultaneously, there is a vast number of possible glycan isomers [16], and many of the powerful tools used to sequence proteins are not able to distinguish the subtle differences between them, making their structural characterization substantially more complicated.

Given the importance of glycans in biological systems and the complexity of determining their primary structure, the development of new tools for the structural characterization of glycans is vital. A 2012 report of the National Research Council of the United States National Academy of Sciences entitled: *Transforming Glycoscience: A roadmap for the future* [5], which analyzed the state of glycan research, recommended that all US funding agencies make "high-resolution of structure determination of carbohydrate structures and complex mixtures" a high priority. Among the roadmap goals of this report is to develop within ten years "the ability to routinely determine the complete carbohydrate structure of any glycan or polymer repeat sequence including branching, anomeric linkages between glycans, and substituents." To achieve this goal, the report called for the "development of new structural techniques", particularly those that "use completely novel approaches to primary structure determination".

Existing Techniques for Glycan Analysis

Glycans can be analyzed in various forms—attached to proteins, attached to peptides, or as free oligosaccharides after enzymatic or chemical release. Since our approach seeks to analyze released glycans, we consider here only those techniques applied to the liberated species.

The inherent complexity of glycan analysis has led to the use of many different experimental approaches [17-19]. Some techniques, such as NMR [20-22] and X-ray crystallography [23], can be extremely valuable for glycan structural analysis, but they are difficult to implement in a high-throughput manner and require considerable amounts of sample. The most commonly used techniques fall into several categories: chromatographic techniques [17, 24-27], electrophoretic techniques [28-30], mass spectrometry [31-

36], ion mobility [37-44] and enzymatic degradation [45]. Because no one method alone can distinguish all the various forms of isomerism present in glycans, it is typical, if not necessary, to combine at least two of them to get the desired information.

One of the most commonly used chromatographic techniques for glycan analysis is hydrophilic interaction liquid chromatography (HILIC) [27, 46], which uses a polar stationary phase and a highly organic mobile phase. Because retention is based on the hydrophilic properties of the analytes, this approach can distinguish many, though not all, of the isomeric forms of glycans. Used as a stand-alone technique, one typically derivatizes the molecule with a fluorophore and uses laser-induced fluorescence (LIF) to increase the detection sensitivity. As with many other chromatographic techniques, the retention time is calibrated with respect to a dextran ladder as an external standard, and comparison to databases can be used to identify the analytes. To confirm the structural assignments of this approach and to use it for sequencing, it can be combined with exoglycosidase digestion [17, 47, 48]. Another way to use HILIC is to combine it with mass spectrometric detection [46, 49], which obviates the need for derivatization. Moreover, the high organic content of the mobile phase makes particularly compatible with electrospray ionization. A major drawback of this approach is the relatively long retention times required for each analysis.

Mass spectrometry has become a major tool for glycan analysis due to its speed and sensitivity [31-36]. Obtaining structural information requires the use of tandem MS techniques, and these have employed a variety of different dissociation methods to generate the cross-ring fragments needed to determine linkage positions and stereochemistry. While permethylation of the free hydroxyl groups prior to fragmentation helps to reveal the locations of the glycosidic bonds, on its own, MS cannot distinguish all of the various glycan isomers. Mass spectrometry has been combined with both chromatographic methods [13, 50, 51] and enzymatic degradation techniques [52] to provide more complete structural characterization, but coupling these methods is not always straightforward and often requires additional steps, which makes it difficult to do high-throughput screening of glycans. In contrast, ion mobility spectrometry (IMS), which separates gas-phase ions based on their average collisional cross section (CCS) on a millisecond timescale, is easily coupled to MS, and several studies have shown that this combination (i.e., IMS-MS) can resolve many of the glycan isomers that are indistinguishable by MS alone [37-44]. Nevertheless, IMS is blind to many of the subtle structural details that distinguish isomeric glycans [39].

One other possibility is to add a spectroscopic dimension to IMS-MS to achieve further isomer discrimination, since spectroscopic fingerprints can be extremely sensitive to the slightest differences between molecules. In this direction, several groups have successfully combined IMS-MS with infrared multi-photon dissociation (IRMPD) spectroscopy for identification of small glycans [53-57], but the room temperature IRMPD spectra are too broad to uniquely identify isomeric disaccharides in a mixture. In very recent work, Mucha et al. [58] used a free-electron laser to obtain spectroscopic fingerprints of oligosaccharides cooled in liquid helium droplets and demonstrated that sufficiently resolved spectra could indeed distinguish the various types of isomerism, albeit with an extremely complex experimental set-up that would be impractical as a broadly used tool. Moreover, the non-linear nature of their spectroscopic technique would complicate the comparison of data across different platforms.

In light of these deficiencies of the state of the art using spectrometry for molecule analysis, substantially improved methods, devices, and systems for molecule analysis, in particular glycan analysis are strongly desired.

SUMMARY

According to one aspect of the present invention, a method is provided for analyzing glycans with cryogenic vibrational spectroscopy, preferably comprising the steps of submitting the glycans to an ionizing process to obtain ions; drawing the ions into a vacuum; injecting the ions into an ion mobility section and grouping them in packets, either before or after injection; and in the ion mobility section spatially separating the ions of the packet into subpackets according to their collisional cross section (CCS), and recompressing the subpackets, by removing an empty space between them by a compression ratio ion mobility programming. The method further preferably comprises loading the ions into a cryogenic ion trap by keeping subpackets with different collisional cross section in respective separate compartments; cooling the ions in collisions with a buffer gas; tagging the ions by attaching one or more messenger molecules and obtaining a weakly bound complex; sending a pulse of infrared light down an axis of the trap to excite vibrations of the cold, trapped, and messenger-tagged ions, and separately ejecting ion subpackets from the trap into an extraction region of a time-of-flight mass spectrometer and measuring the number of remaining messenger-tagged ions and untagged ions for the subpacket.

Moreover, according to another aspect of the present invention, a system for analyzing a plurality of molecules with cryogenic vibrational spectroscopy. Preferably, the system includes a structure for lossless ion manipulations (SLIM) including an ion mobility section for receiving a packet of molecules in a ionized form, the SLIM configured for spatially separating the ions of the packet into subpackets according to a collisional cross section (CCS) of the ions, for keeping subpackets with different CCS in a respective separate compartment, and for recompressing the subpackets by removing an empty space between them, a cryogenic ion trap for cooling the ions in collision with a buffer gas and for tagging the ions by attaching a messenger molecule, an optical light source providing an infrared light to the cryogenic ion trap to excite vibrations of the cold, trapped, and messenger-tagged ions, and a time-of-flight mass spectrometer having an extraction region for separately receiving ion subpackets from the cryogenic ion trap for measuring the number of remaining messenger-tagged ions and untagged ions for each subpacket.

In a preferred embodiment, the method further comprises varying the wavelength of the infrared light pulse and repeating the above-mentioned measurement to generate an infrared spectrum of each subpacket of ions.

In a further preferred embodiment, the method further comprises measuring an ion drift time, a mass, and an infrared spectrum for each ion subpacket, comparing the data obtained from the measurements to entries of a determined database to identify species of the glycans.

In a further preferred embodiment, the method comprises fragmenting a parent glycan ion and applying the method to simultaneously measure the drift time, mass, and infrared spectrum of the resulting fragments.

Despite the great promise of high-resolution vibrational spectroscopy for glycan identification, there is one major drawback with the state of the art approach. By adding a spectroscopic dimension to mass spectrometry and ion mobility one increases the measurement time, since this approach requires scanning the infrared laser frequency across the spectrum, which can take as long as twenty (20) minutes for each species to achieve a sufficient signal-to-noise ratio. The total time required to measure a complex mixture that might include 20-30 different glycans would thus hamper its use as an analytical tool.

As described in detail below, according to an aspect of the present invention, the designing and constructing an device is provided that will overcome this limitation by multiplexing the measurement of mass, CCS (via ion mobility) and cryogenic vibrational fingerprint spectra of many species simultaneously, greatly reducing the average measurement time. Moreover, this approach will eliminate the time-consuming chromatographic separations and chemical derivatization steps often used in glycan analysis. Therefore, the resulting high-throughput analytical tool for glycan identification represents a tremendous breakthrough for the field of glycoscience.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The above and other objects, features and advantages of the present invention and the manner of realizing them will become more apparent, and the invention itself will best be understood from a study of the following description with reference to the attached drawings showing some preferred embodiments of the invention.

DETAILED DESCRIPTION OF THE PREFERRED EMBODIMENTS

Figure 1:
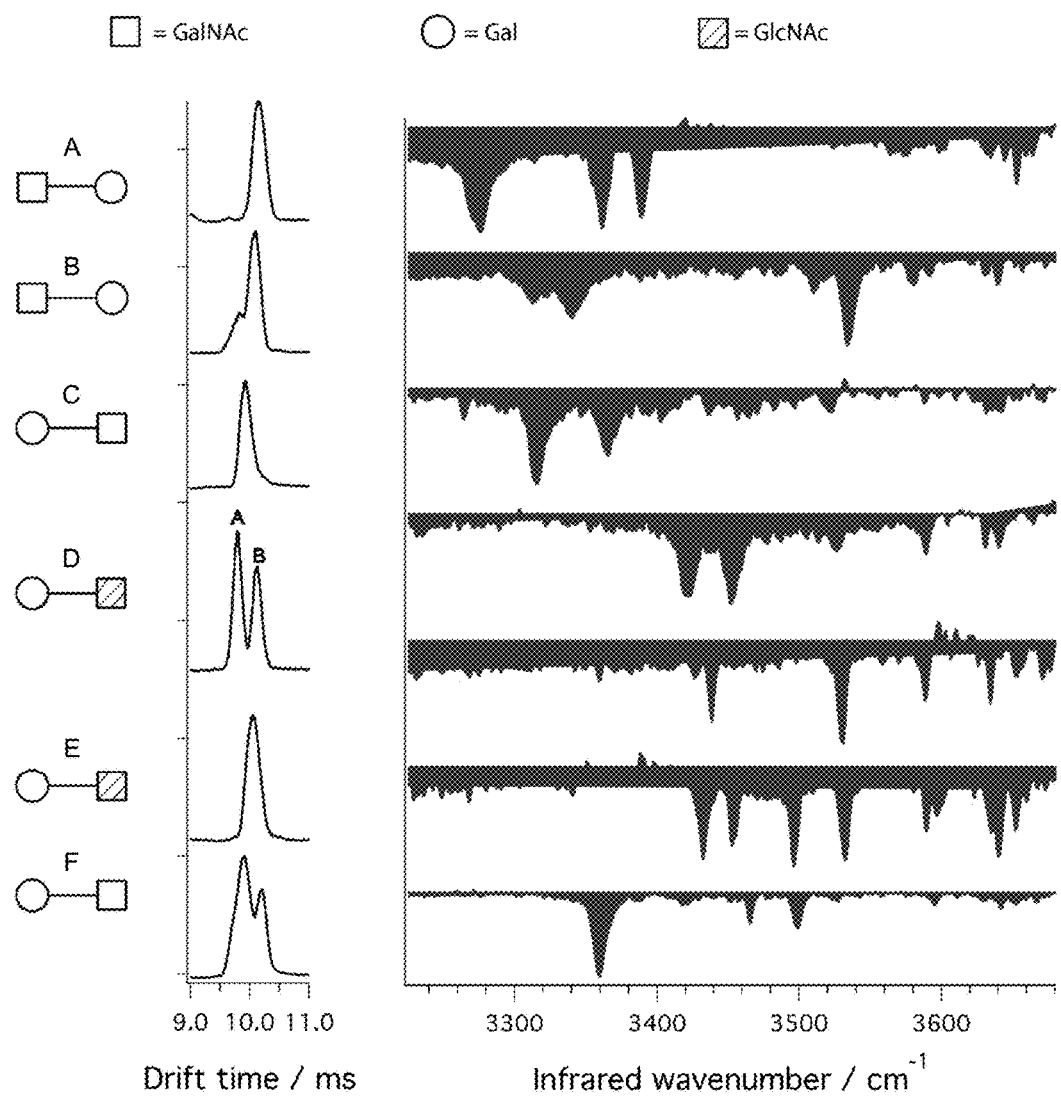
FIG. 1 schematically shows fingerprint vibrational spectra and arrival-time distributions for six isomeric disaccharides that differ in their anomericity with element A vs B; sequence order of element B versus C; attachment point of element D versus E; and monosaccharide content of element E versus F. The two vibrational spectra in element D correspond to two stable conformations that do not interconvert upon annealing. The infrared spectra were obtained by cryogenic, messenger-tagging spectroscopy [59]

Glycans, or oligosaccharides, are ubiquitous in biological systems. Because they decorate the surface of cells, they play a key role in virtually all cellular recognition processes and are implicated in almost every major disease. Despite their importance, the characterization of glycan primary structure lags far behind that of proteins and DNA because of their intrinsic isomeric complexity. The isomeric nature of the monosaccharide building blocks, the stereochemistry of the glycosidic bond, the possibility of multiple attachment points, and the occurrence of isomeric branched structures all make glycans difficult to analyze.

Although mass spectrometry (MS) is one of the most sensitive approaches for glycan analysis, it has difficulty to distinguish all these various types of isomerisms. Ion mobility spectrometry (IMS) combined with MS has demonstrated some ability to identify glycan anomers and regioisomers, but cannot easily distinguish isomeric disaccharides, for example.

It has recently been recently demonstrated that cryogenic infrared spectroscopy provides unique vibrational fingerprints of glycans that distinguishes all the various types of isomerism. When combined with simultaneous measurements of mass and ion mobility, these fingerprints can be tabulated in a database and used to identify a given glycan from a mixture. However, adding a spectroscopic dimension to ion mobility and mass measurements requires additional time, which hampers it use as an analytical tool. To use spectroscopic data for real-world glycan analysis, one must multiplex the measurement process and record the vibrational spectrum of many species simultaneously.

According to one aspect of the present invention, the goal is to provide a novel, transformative approach to molecular analysis, more particularly glycan structural analysis. As described further below, we have recently demonstrated that cryogenic, messenger-tagging spectroscopy, when combined with IMS-MS, is a powerful tool to distinguish even the slightest structural difference between glycan isomers [59, 60]. The high level of isomer discrimination of this approach comes from the detailed nature of the spectral fingerprint measured at low temperatures. When combined with simultaneous measurements of mass and ion mobility, these fingerprints can be tabulated in a database and used to identify a given glycan, either isolated by itself or in a mixture.

According to one aspect of the present invention, an instrument has been designed and constructed that combines state-of-the-art ion mobility separation, cryogenic ion spectroscopy, and time-of-flight mass spectrometry to perform high throughput analysis of glycan primary structure, for example as a device, a system, and a method.

One goal of the present invention is to be able to take a mixture of glycans isolated from a natural source and identify all if its constituents, including the specification of the monosaccharide content, the linkage positions and stereochemistry, branching patterns, and substitution sites of each species. To achieve this goal, a novel, high-throughput method and system has been developed for analyzing glycan primary structure that combines state-of-the-art ion mobility spectrometry with cryogenic vibrational spectroscopy and time-of-flight mass spectrometry into a single instrument. The measured data, which will include the mass, collisional cross section, and cryogenic vibrational spectrum of each species, will provide a unique fingerprint of individual glycans that will be tabulated in a database and used for identification. High-throughput will be achieved by multiplexing the spectral measurements of all species in a way that preserves information obtained by ion mobility separation.

The implementation these aspects of the invention, as a method and corresponding system, represents a tremendous breakthrough for glycoscience, providing in a powerful new tool for fundamental research in chemical and molecular biology and a practical diagnostic for the pharmaceutical industry.

Methodology

Introduction

Our proposed method for performing high-throughput analysis of glycan primary structure is based on a series of proof-of-principle experiments [59, 60]. As shown in FIG. 1 for a series of isomeric disaccharides, infrared spectra in the OH stretching region provide a unique fingerprint of a given glycan that is exquisitely sensitive to slightest differences in its structure, even in cases where ion mobility cannot distinguish them. Differences in anomericity of the glycosidic bond, the attachment point between monosaccharides, the sequence order, or even in the change in orientation of a single stereogenic center produces dramatic changes in the pattern of vibrational bands that are straightforward to detect. This should not be surprising. The OH groups of a glycan molecule have large dipole moments that interact with each other through dipole-dipole forces. Even weak interactions will cause the vibrational frequencies of the hydroxyl groups to shift, and given the high resolution of spectra taken under cryogenic conditions, one can easily measure these shifts. Changing the orientation of a particular stereogenic center, for example, changes the entire coupled network, reflecting itself in a change in the vibrational fingerprint. Together with a measurement of the glycan mass and its average cross section (i.e., by ion mobility), these vibrational fingerprints provide a unique identifier for a given glycan molecule.

As promising as these proof-of-principle experiments are, there are several requirements for making them into a widely accessible analytical technique.

1. The measurements must be performed rapidly, with high-throughput, to provide a sufficiently significant advantage over existing techniques.
2. Vibrational spectra of larger glycans must exhibit sufficiently distinct spectral fingerprints that can serve as a unique identifier of the molecule.
3. One must be able to construct a functional database using known standards in a reasonable amount of time.
4. There must a mechanism to analyze unknown species (i.e., those that we do not find in our database) and add them to the database.
5. Given a mixture of isomeric glycan species that are not resolved by ion mobility separation, one must be able to decompose the measured spectra into those of its constituents and from this determine the relative concentrations.
6. The measurements need to be robust and insensitive to small changes in the experimental conditions so that they can be performed in a properly equipped laboratory.

Details of the method and system are described hereinafter, including its capabilities with the above-discussed issues in mind.

Overview of the Experimental Approach

Figure 2:
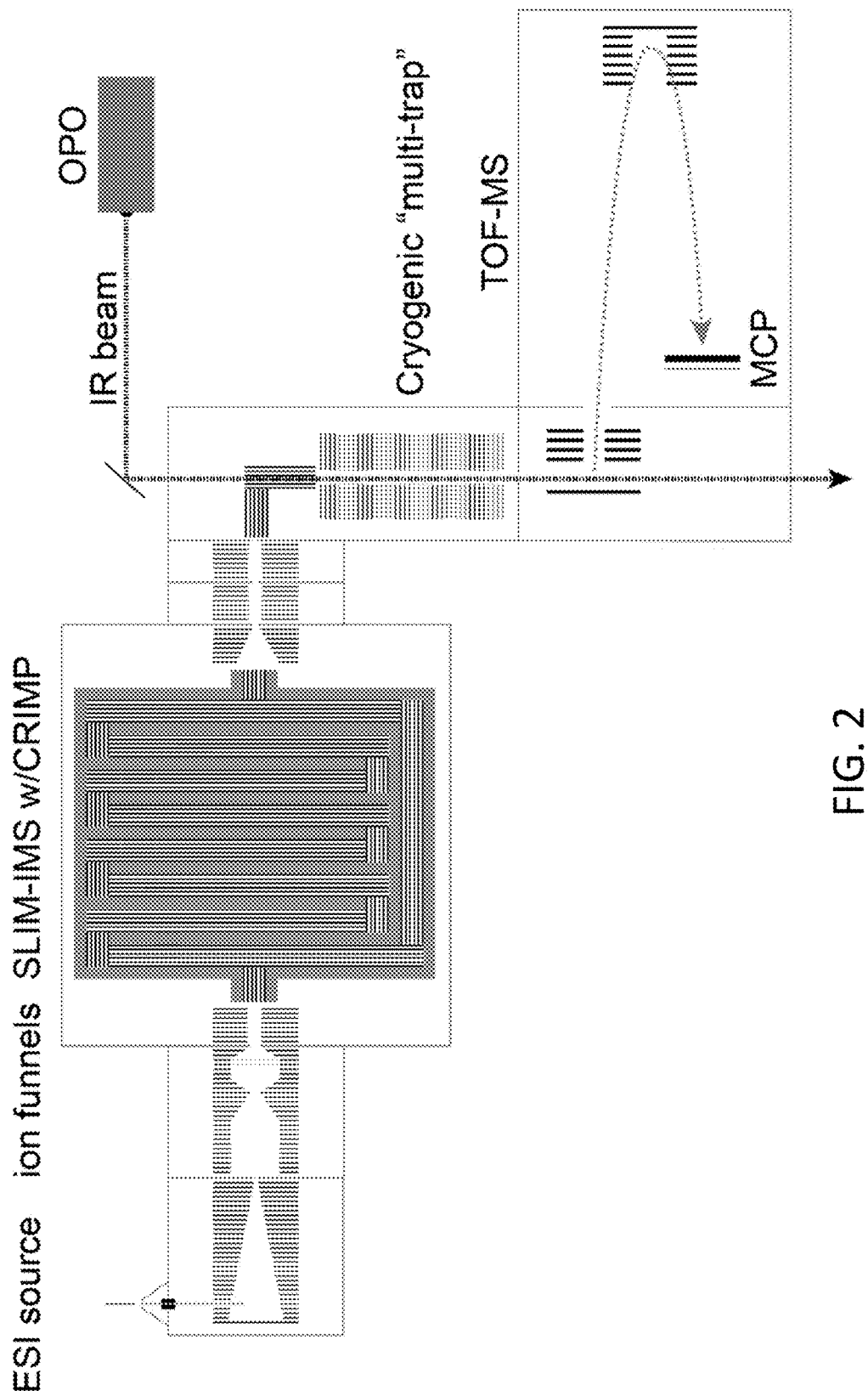
FIG. 2 shows a schematic overview of the device for an experimental approach.

While our proof-of-principle experiments demonstrate that cryogenic vibrational spectroscopy provides unique fingerprints of individual glycans, a number of new technologies need to be introduced to make this approach into an analytically useful, high-throughput tool for glycan analysis. We first give an overview of our next-generation instrument, shown schematically in FIG. 2, and then provide details on the features that make these new experiments possible.

Ions generated by nano-electrospray will be drawn into vacuum through a heated capillary and enter a series of ion funnels, which focus the ions before injecting a packet of them into the ion mobility section of the instrument. Rather than use a standard ion-mobility drift-tube as in our proof-of-principle experiments, we will employ technology developed by Smith and coworkers called Structures for Lossless Ion Manipulations (SLIM) [61, 63-68], which uses printed circuit board electrodes to perform ion mobility separations. The SLIM is also described in U.S. Pat. No. 8,835,839, U.S. Patent Publication No. 2016/0071715, and International Patent Publication No. PCT/US2015/048038, these three references herewith incorporated by reference in their entirety. The ions will be spatially separated on the SLIM board according to their collisional cross section (CCS). As explained in more detail below, they will then enter a section of the board that recompresses the separated packets and removes the empty space between them, using a technique called compression ratio ion mobility programming (CRIMP) [69]. While it may seem counter-intuitive to separate the ions according to their CCS and then recompress them, the reason for this will soon become clear.

After compressing the mobility distribution, all the ions will be loaded into a cryogenic ion trap in a way that keeps the packets with different CCS in separate compartments. Once there, they will be cooled in collisions with cold $N_2$ buffer gas and tagged by attaching an $N_2$ molecule to form a weakly bound complex. A pulse of infrared light from an optical parametric oscillator (OPO) will be sent down the axis of the trap to excite vibrations of the cold, trapped, messenger-tagged ions. If a molecule in the trap absorbs an infrared photon, energy will be rapidly redistributed throughout its vibrational degrees of freedom, warming it up and knocking off the $N_2$ tag. Each ion packet will then be separately ejected from the trap and sent into the extraction region of a time-of-flight mass spectrometer. Pulsing the extraction electrodes will send both tagged and untagged ions into a TOF drift tube, where their time of flight (and hence their mass) will be measured, and the fraction of ions that have absorbed a photon and lost its tag will be determined from the ion signals at the relevant flight times. The process of ejecting a packet of mobility-separated ions from the cryogenic ion trap into the TOF-MS will be repeated rapidly until all the packets have been analyzed. Because ion extraction from the trap and the ensuing TOF measurement can be done at a repetition rate of greater than 1 kHz, all the ion packets in the trap can be analyzed in the 100 ms between pulses of the infrared OPO. The wavenumber of the OPO is then incremented, and the entire cycle is repeated. In this way, the ion drift time (which can be converted to cross section), the mass, and the infrared spectrum is measured for each ion packet in our sample. We will then compare this data to entries in a database to identify the species in our sample. If there are isomers that have not been separated by their CCS, we will use the spectra in the database to decompose the spectrum of the mixture and determine its principal components.

Next, each part of the process and method is described in detail.

Details of the Experimental Approach (i) Ion Mobility Separation Using SLIM

Figure 3:
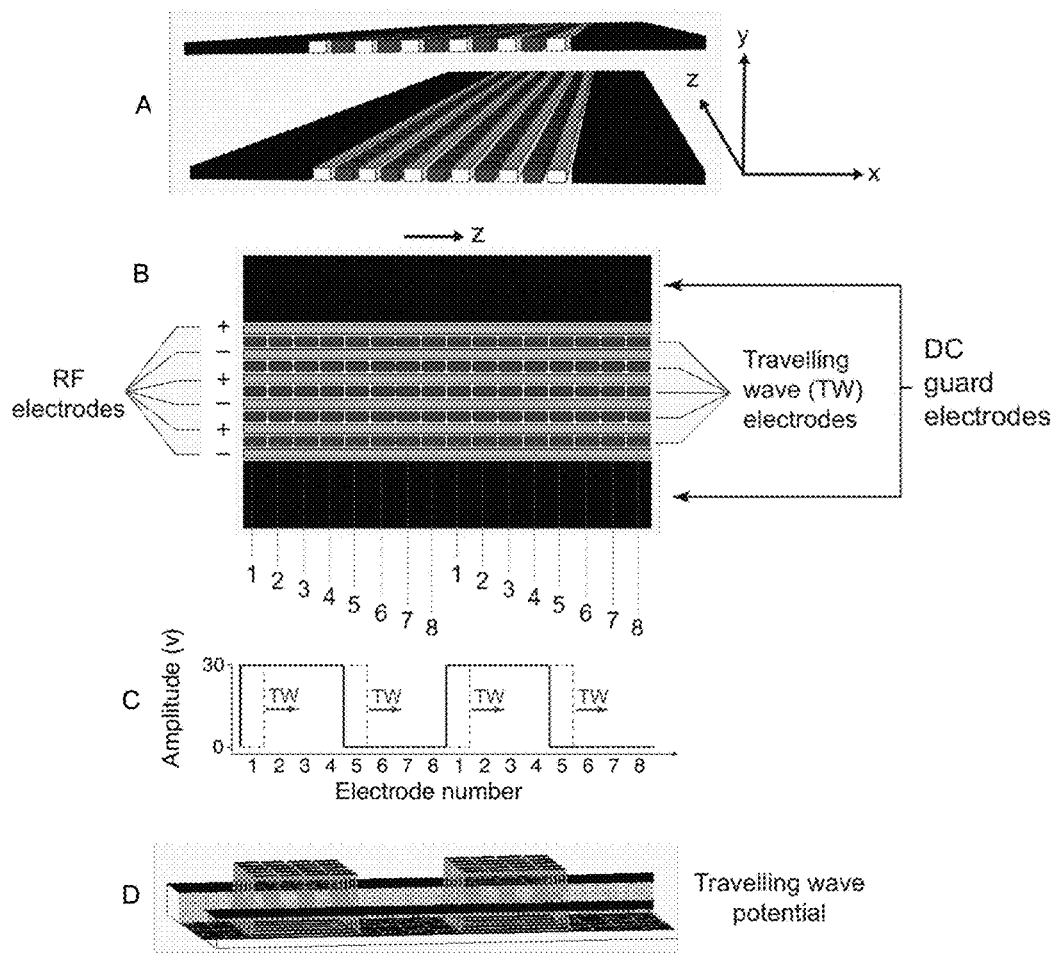
FIG. 3 shows a schematic of the basic unit of a Structures for Lossless Ion Manipulations (SLIM) module. Element A showing the sandwich of two printed circuit (PC) boards that form the separation channel; element B showing the various traces on the PC boards; elements C and D the traveling wave potential. Elements B and C were adapted from Reference [61]
Figure 4:
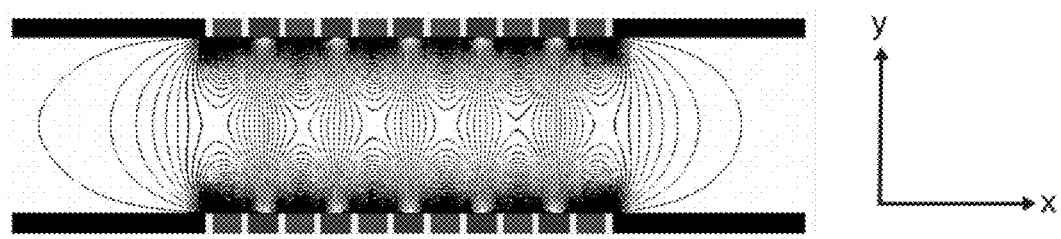
FIG. 4 shows a field created by the radio-frequency (RF) electrodes in the x-y plane.

The SLIM technology [61, 63-68] is a type of travelling wave ion mobility that uses a "sandwich" of two opposing PC board electrodes, not unlike those we currently use in our cryogenic ion trap [70]. The basic unit of a SLIM module is illustrated in FIG. 3 (adapted from Ref. [61]). Element A of FIG. 3 shows the two PC boards that form the channel in which the ions move. In the example shown, each board includes eleven (11) separate tracks, as shown in B of FIG. 3: six of which carry alternate phases of an RF potential and confine the ions in the y-direction, and five of which carry the travelling wave that pushes ions in the z-direction. On either side of these eleven tracks are DC guard electrodes that confine the ions in the x-direction. As shown in B and C of FIG. 3, the travelling wave (TW) is made by a repeating sequence of eight DC pads, four of which at any moment are at a high potential and the other four are at low potential. The wave "travels" by dropping the potential of pad 1 from high to low and raising the potential of pad 5 from low to high as shown in C of FIG. 3. Because the sequence is repeated, pads on the corresponding units along the track are wired together. The travelling wave potential is shown in element D of FIG. 3. FIG. 4 shows the RF potential in the x-y plane, which forms channels in the x-direction through which the ions propagate.

As in all types of travelling wave ion mobility, ions of different collisional cross section are separated as they roll over from one potential well to the next because of different drag forces through the bath gas. The degree of separation depends upon the height and propagation speed of the travelling wave as well as the length over which the ions are propagated.

Figure 5:
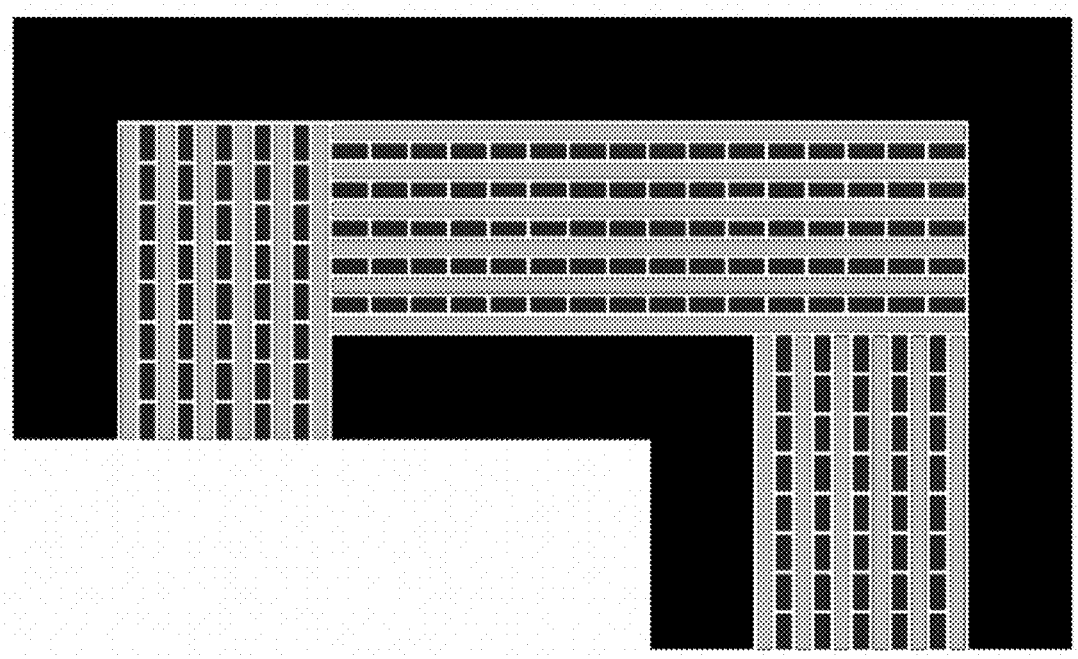
FIG. 5 shows a section of a SLIM module incorporating turns.

Smith and coworkers have demonstrated that one can used these SLIM tracks to direct ions around turns [67], as shown in FIG. 5, which allows one to create serpentine paths that can extend the overall separation length on a board of moderate size [65]. For example, on a board measuring 45.9 cm×32.5 cm, a path length of thirteen (13) meters has been achieved [65].

Figure 6:
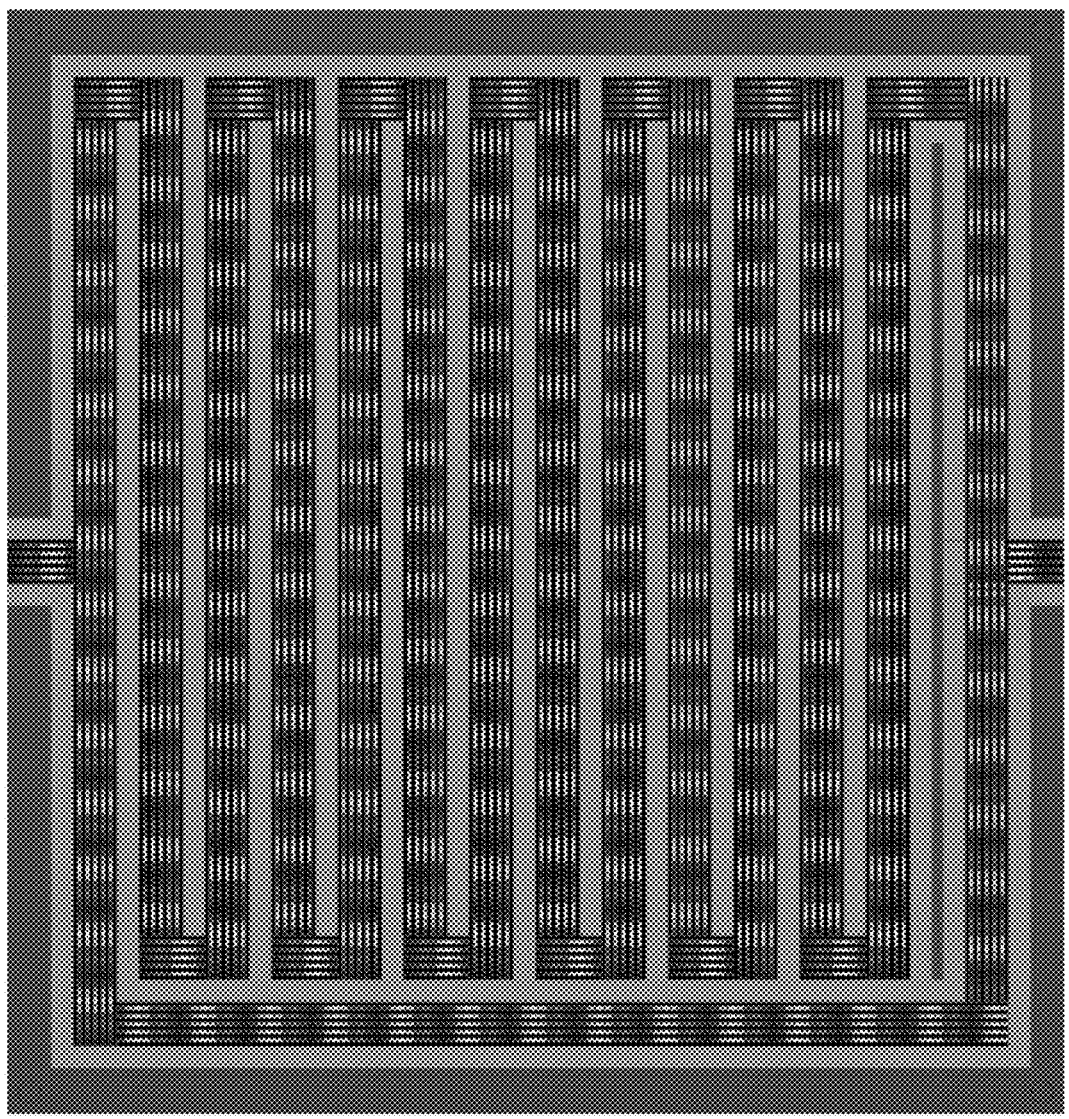
FIG. 6 shows a serpentine SLIM board with the possibility of switching the ions to make addition round trips before exiting.

In additions to turns, they have also introduced T-shaped switches that can eject ions from a track onto a perpendicular one. Using these switches, one can cause ions to traverse a serpentine path multiple times before switching them out for detection, further extending the path length and increasing the resolution [67]. We have designed a SLIM board that allows for such manipulations, shown in FIG. 6, and have used SIMION to simulate ion trajectories, demonstrating that we can both turn and switch ions.

The use of SLIM technology has several advantages for the proposed experiments:

a) Like our planar ion trap, PCB electrodes are easy to fabricate and assemble. They can also be easily interchanged.

b) SLIM uses low-voltage travelling waves, avoiding the need to maintain a high voltage across the length of a traditional linear drift tube.

c) The ion transmission efficiency of SLIM devices is very high, and this will increase the sensitivity for low abundant species and decrease the overall data collection time compared to our proof-of-principle experiments.

d) The long effective path length and resulting high resolution achievable using SLIM [63-65] will help distinguish similar glycan structures. This will simplify the use of spectroscopy to identify isomers in that fewer of them will overlap in the mobility dimension.

e) A SLIM separation device is compact, reducing the overall size of the instrument. This also makes it easier to cool compared to a normal ion mobility drift tube, which further increases the resolution.

f) Once ions are separated by their mobility, they can be easily manipulated in traveling traps in such a way that keeps them separate.

According to an aspect of the present invention, a high-throughput approach is provided that enables substantial advantages over the state of the art. Once ions are separated by their mobility in the SLIM device, one can raise the potential of the travelling waves and turn them into travelling traps, which no longer achieve separation, since the ions simply surf on the potential wall without exiting the trap. This allows us to direct the ions wherever we want and at the same time maintain them in separated packets according to their CCS. Moreover, because the separation process is "digital", we can keep track of every trap and determine exactly which ones include ions. As described below, obtaining information from a "pre-scan" in which the arrival time distribution is measured and which traps include ions is determined provides for an aspect to making multiplexed measurements of vibrational spectra.

(ii) The Compression Ratio Ion Mobility Programming (CRIMP) Technique—an Aspect of the Multiplexing After having measured the mobility of the ions (i.e., their CCS via their arrival-time) on a SLIM board, we want to measure their fingerprint vibrational spectrum and their mass while retaining the information we have already obtained on their mobility. Moreover, we want to be able to do this in a multiplexed manner, so that we measure the spectrum of molecules of all CCS and all masses in the same experiment.

To do this, information from an ion mobility "pre-scan" can be used to determine which cells include ions. In general, these ions will be separated in space. For example, if we have an effective path length of several meters on our SLIM separation board, it is entirely conceivable that ion packets may be spatially separated by as much as a meter. To be able to multiplex a spectroscopic measurement of ions separated so distant in space, we need a way to bring them together—otherwise the length of the ion trap would be impractical. The solution to this problem is to use the technique called compression ratio ion mobility programming (CRIMP) [69], albeit in a mode not yet demonstrated by the Smith group.

Figure 7:
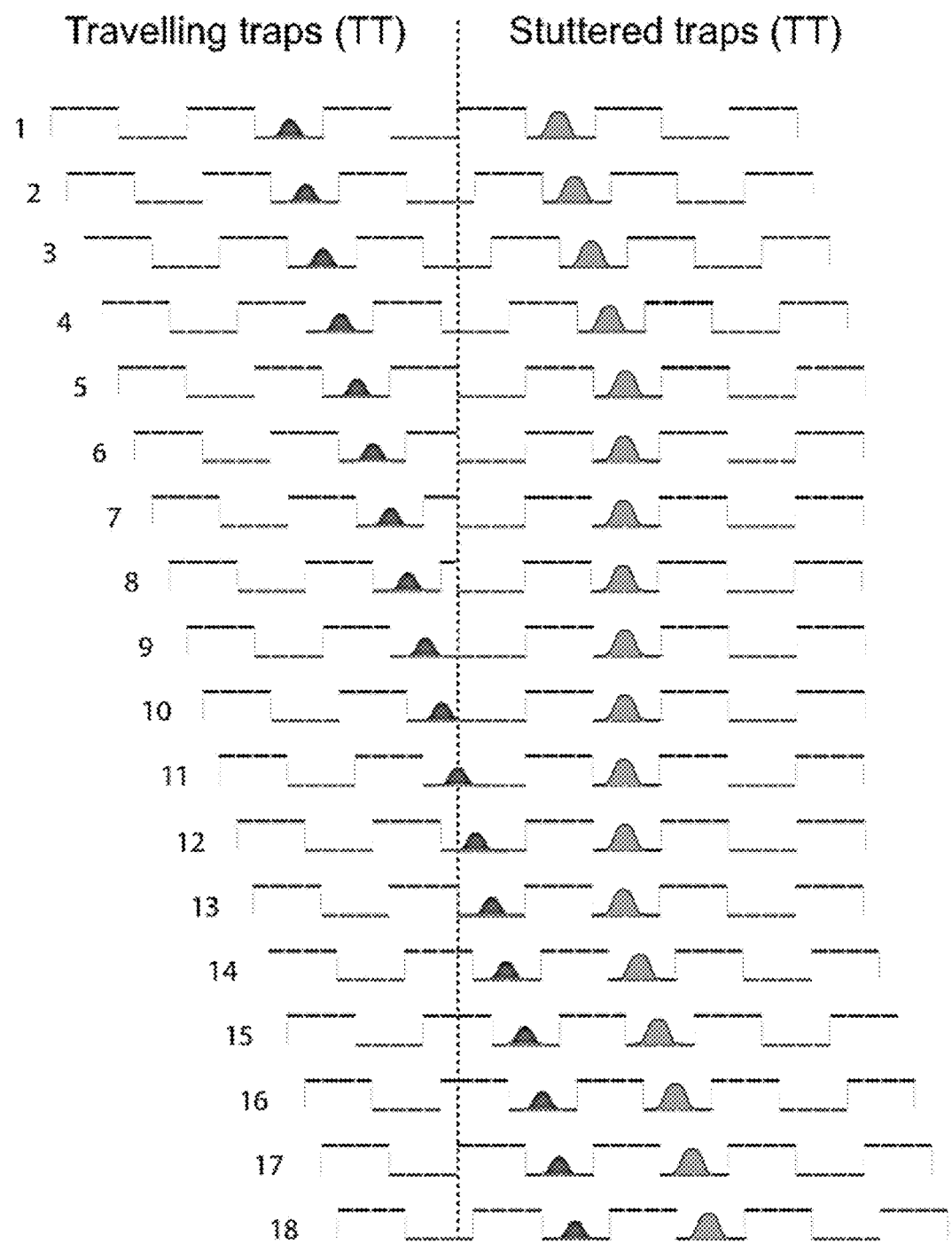
FIG. 7 shows a principle of compression ratio ion mobility programming (CRIMP). Two separate sections of the SLIM board are wired such that one can control the advancement of the travelling wave independently. In this example, at time steps 1-5, the travelling wave advances at the same rate on both sections of the board. At time steps 6-13, the stuttered traps (ST) don't advance, while the travelling traps (TT) advance at the same constant rate. At time steps 14-18 the ST begin to advance again at the same rate as the TT. The net result is that ion packets that were separated in space have now been put into adjacent traps.

The basic principle of CRIMP is illustrated schematically in FIG. 7. Ions that have been separated by their mobility can have their separation locked in by increasing the potential of the travelling waves, putting them in what are called traveling traps (TT). The CRIMP technique allows one to combine any number of adjacent traps at the interface of a separate section of the SLIM board that has traveling traps moving at a different speed, which are called stuttered traps (ST). Basically, the ratio of the speed of the traveling traps to the average speed of the stuttered traps define a compression ratio, which in principle is only limited if one reaches the space-charge limit of a particular trap.

Figure 8:
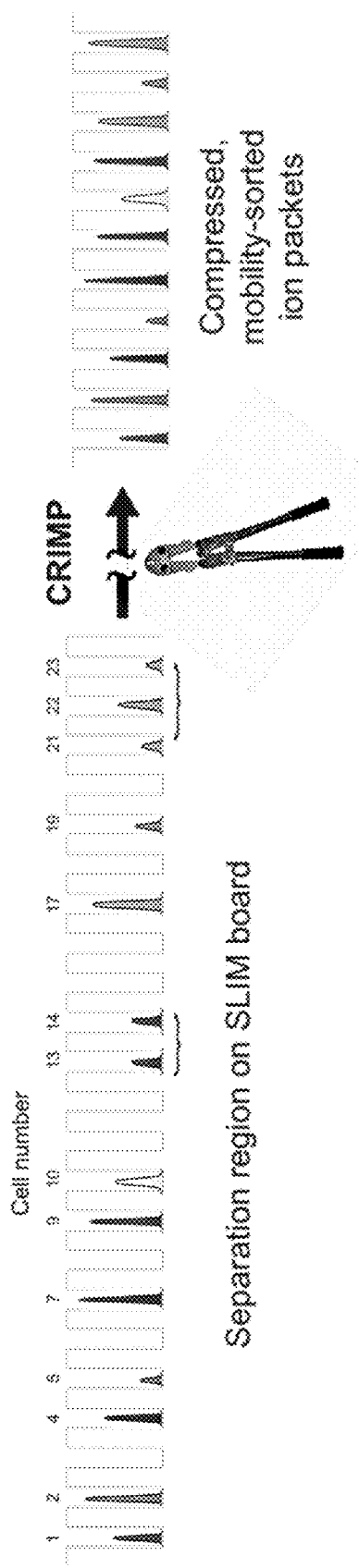
FIG. 8 shows a representation of the method using the CRIMP technique to take mobility-sorted ions and put them into adjacent travelling traps.

While current implementations of CRIMP use a fixed compression ratio [69], we will implement it slightly differently. We will use knowledge from a pre-scan of the ion arrival-time distribution to determine which cells have ions in them. Based on this pre-scan, the advancement of the stuttered traps will be programed so as to remove all the empty cells between ion packets, as illustrated schematically in FIG. 8. On the left are ions separated by SLIM, which are being transported in travelling traps. Some ion packets may be confined to a single trap, although in general, most mobility peaks will be spread out among multiple adjacent traps, as illustrated for cells 13-14 and 21-23. By knowing which cells we want to combine, we can program the ST to move in such a way that eliminates all empty cells and stores ions of different mobility in adjacent TT.

It should be emphasized that although we have compressed the arrival time distribution in space, we have maintained the separation of ions according to their mobility, and we know the CCS of each ion packet from our pre-scan. The next step is to load the mobility-sorted ions into our cryogenic ion trap, cool them, measure their infrared spectrum, and then measure their mass.

(iii) Multiplexed Spectral Measurements and TOF Analysis

Having sorted the glycan molecules by their CCS and put them in adjacent traveling traps on the SLIM board, we will then transfer them through a differential pumping stage into high vacuum. The fields used in the SLIM traveling traps are strong enough to hold them through differential pumping and carry them to a cryogenic ion trap, which will be segmented in the axial direction so that it can include separated packets of ions without scrambling them. For this reason, we refer to it as a cryogenic "multi-trap".

The multi-trap can have various different geometries. One implementation could be a ring-electrode trap [71], which is a cylindrically symmetric RF device with an effective radial field determined by the ring spacing. A schematic of such a device is shown in FIG. 9.

Figure 10:
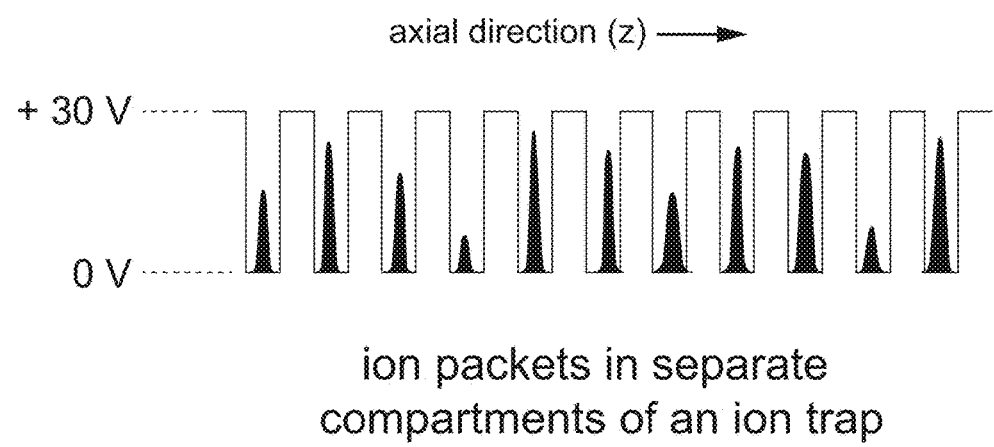
FIG. 10 depicts schematic showing ions trapped in separate compartments in the axial direction of the cylindrical electrode trap shown in FIG. 9.

Opposite phases of an RF voltage are applied to alternate rings, confining the ions in the radial direction [71]. Moreover, because one can control the DC bias on each ring, one can use them as traps in the axial dimension as shown schematically below in FIG. 10.

Figure 9:
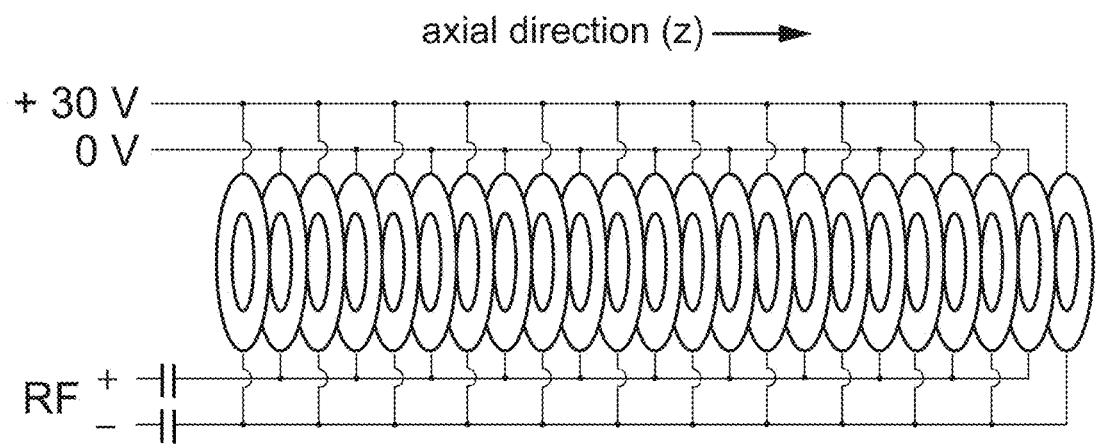
FIG. 9 exemplarily shows a ring electrode trap used to confine ions radially and trap them axially in separate compartments.

In actual operation, one would control the DC levels of each ring of the trap in FIG. 9 separately rather than tying every second one together, since this would be needed for loading and unloading.

Figure 11:
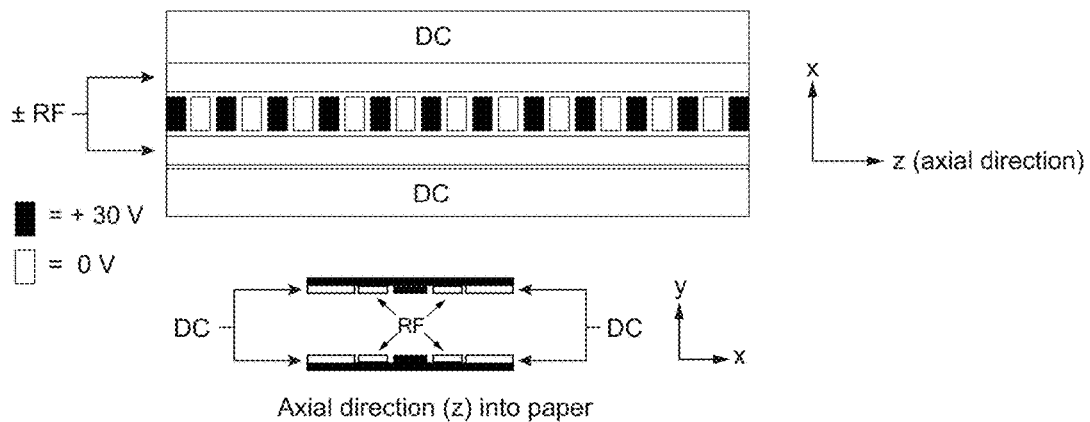
FIG. 11 shows a planar implementation of the multi-trap.

Another implementation of the multi-trap would be to use a planar geometry, as illustrated in FIG. 11 below. In this exemplary case, the trap includes a sandwich of two printed circuit boards (PCB). A DC potential would be applied to the outermost stripes to confine the ions in the x-direction. The RF stripes on each board would have opposite phases of an RF potential, and this would serve to confine the ions in the y-direction. The z (axial) dimension would provide the separate compartments by applying different DC voltages on alternating pads in the center of the board, producing a potential in the axial dimension that resembles that of FIG. 10. Once again, in practice, the actual DC potentials of the center stripe would each be controlled separately to facilitate loading and unloading.

Figure 12:
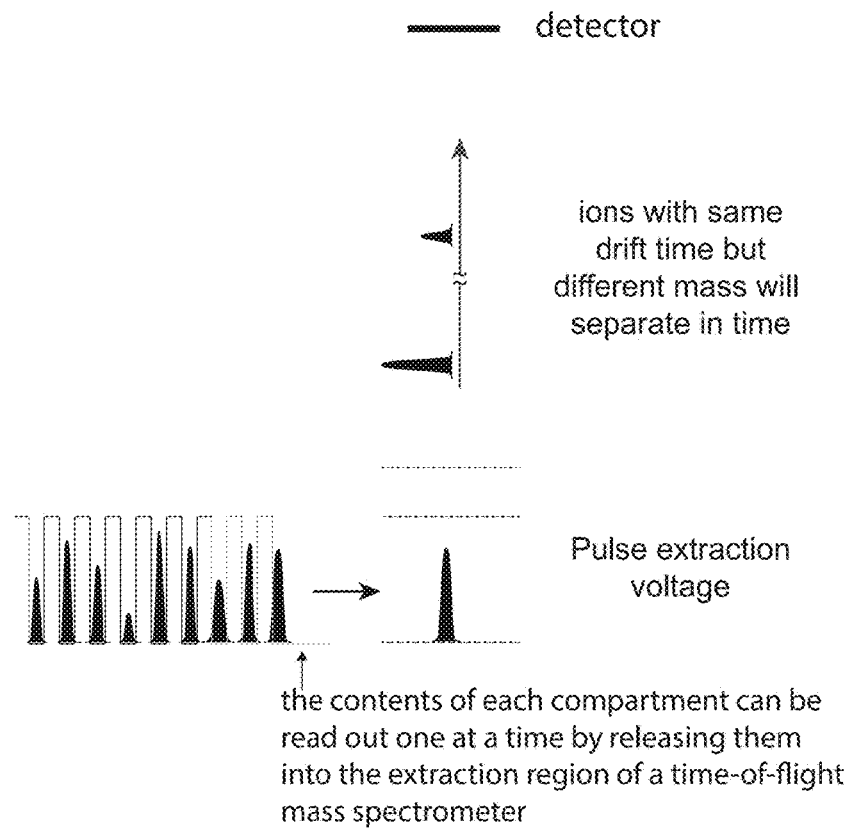
FIG. 12 provides for a schematic illustrating the sequential read-out of each compartment of the multi-trap by injecting them into the extraction region of a time-of-flight mass spectrometer and pulsing the extraction electrodes.

Having ions of different mobility in separate compartments in the axial dimension of our multi-trap allows to multiplex the spectral measurements of all the ions, and this one aspect of to the high-throughput nature of the present method and system. Having loaded the multi-trap with the mobility-separated ions, we pulse in cold $N_2$ buffer gas, which cools the ions and tags them. We then send an infrared pulse from an optical parametric oscillator (OPO) through the trap, simultaneously irradiating all the ions. If a particular tagged ion in the trap absorbs an infrared photon, the energy will rapidly redistribute among the vibrational modes and blow off the weakly bound tag molecule (as in our proof-of-principle experiments). We then eject one packet of mobility-separated ions at a time from the multi-trap and send it into the extraction region of a reflectron TOF-MS, as shown schematically in FIG. 12.

The extraction electrodes are pulsed to send the ions into the TOF drift tube, where the tagged and untagged ions separate in time and are detected. The infrared absorption of a particular ion at the OPO wavelength will be given by the fraction of tagged ion signal that is depleted upon laser excitation. The ejection process is repeated rapidly until all the packets have been analyzed in the same way. Because the process of ion extraction and TOF measurement can be done at a repetition rate of greater than 1 kHz, all the ions in the trap can be analyzed in the 100 ms between pulses of the infrared OPO. The wavenumber of the OPO is then incremented, and the entire cycle is repeated.

If there are species that overlap both in their drift time and their mass, we will separate them based on a decomposition of the vibrational spectrum, using the spectra in our database to determine the principal components.

As an example, for a 15-20 cm ring electrode trap, we estimate that we should be able to fit 15-20 different mobility-separated ion packets in the axial dimension. As there will almost certainly be some isomeric species with overlapping CCS, the total number of species in the trap that we analyze may be as many forty (40). Since the spectrum of each species is measured with one scan of the OPO, this reduces the average measurement time considerably—perhaps less than one minute per species on average.

Once we have obtained the mass, CCS, and infrared spectrum of each species in our sample, we identify them by comparison with a database that we will construct. We discuss the details of this process below.

(iv) A Database Approach to the Determination of Glycan Primary Structure

A. General Philosophy of Using a Database

The usual procedure for determining ion structure from spectroscopy is to measure a high-resolution vibrational spectrum and then compare it with those computed for the lowest-energy structures determined by high-level quantum chemical calculations [70, 72, 73]. Once a sufficiently good match is found, the computed 3D structure is assigned to the molecule. Because we are interested in only the primary (i.e., covalent) structure of glycans, including all the various isomerisms, our approach is completely different. A database for glycans is established including their respective mass, collisional cross section, and vibrational spectrum. Thereafter, an unknown glycan molecule or mixture is identified by measuring these quantities and comparing it with entries in the database. This means that our determination of primary structure does not depend upon high-level quantum chemical calculations, which are extremely difficult for glycans including of more than a few monosaccharide units.

While our approach differs from the standard approach used by the ion spectroscopy community, database approaches have been central to glycan analysis [74-76]. Information from chromatographic techniques [45, 49, 74, 77], mass spectrometry [78], ion mobility [79, 80], and exoglycosidase digestion [48] have all been collected in databases and used in glycan analysis, and we will complement these existing databases by constructing one based on cryogenic vibrational spectroscopy. It would make strategic sense for us to start by targeting glycan molecules that have already been fully characterized by other methods and tabulated in databases, which would relieve the need for us to perform our own sequence analysis based on exoglycosidase degradation. It will be preferable that the results are compared and coordinated with the GlycoMob database of glycan collisional cross sections determined from on mobility [80]. Once we have a full database entry for a particular glycan, we can rapidly identify it in a sample.

Our spectroscopic database will have the important advantage that the vibrational spectrum is an intrinsic property of the molecule that can be reproducibly measured in different laboratories. As long as one is measuring species cooled to sufficiently low temperatures, the linear vibrational spectrum will be the same every time, even under slightly different conditions in different laboratories. The same cannot be said for many other types of tabulated data. For example, measuring chromatographic retention time in glycose units (GU) depends on the properties of the column, and one must calibrate this against a dextran ladder each time. Data from tandem mass spectrometry can differ depending upon the fragmentation technique and the amount of energy imparted. Even ion mobility will depend upon the pressure and temperature of the drift gas, which must be controlled. In contrast, a vibrational spectrum, even if performed on tagged species, is an inherent property of the molecule determined by quantum mechanics, making it much easier to compare from one laboratory to another. The infrared laser source needs to be calibrated, but this is done using a standard wavemeter.

B. The Construction of the Database

Figure 13:
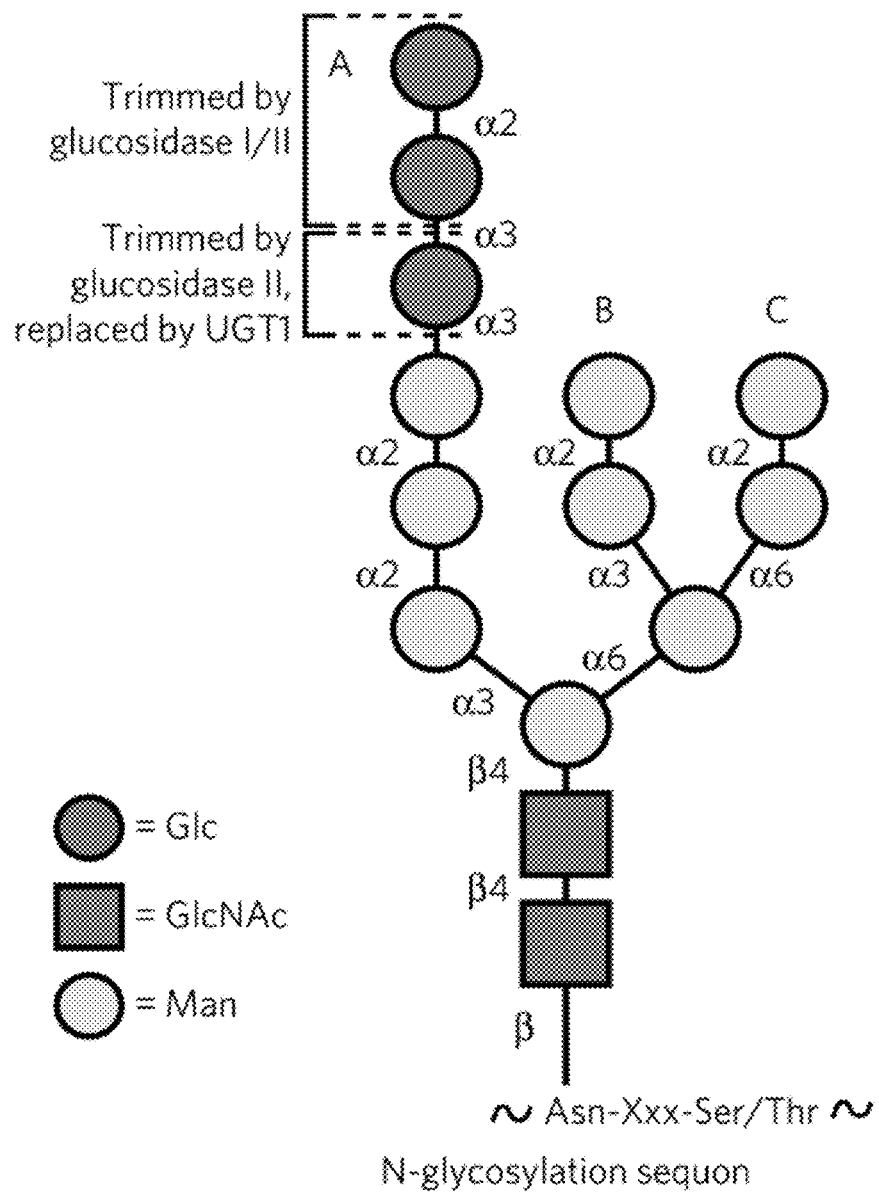
FIG. 13 shows a N-linked glycan unit that is attached to the asparagine sidechain of proteins and then trimmed and modified enzymatically, taken from Reference [62]

Given all of the possible isomeric structures for a glycan of a given mass, it might seem hopeless to try to construct a database large enough to include them all [16]. Fortunately, there are conserved structures, particularly in the case of N-linked glycans, which helps reduce magnitude of the problem. This comes from the way that N-linked glycans are synthesized: a 14-residue unit, shown in FIG. 13, is covalently attached to the asparagine side-chain in the endoplasmic reticulum and then modified enzymatically [81].

Modification of this initial unit is carried out by enzymes that both trim it down but also add additional monosaccharides. After these processing steps, all N-glycans regain a basic core structure including two GlcNAc residues and three (3) mannose residues, as shown in FIG. 14.

Figure 14:
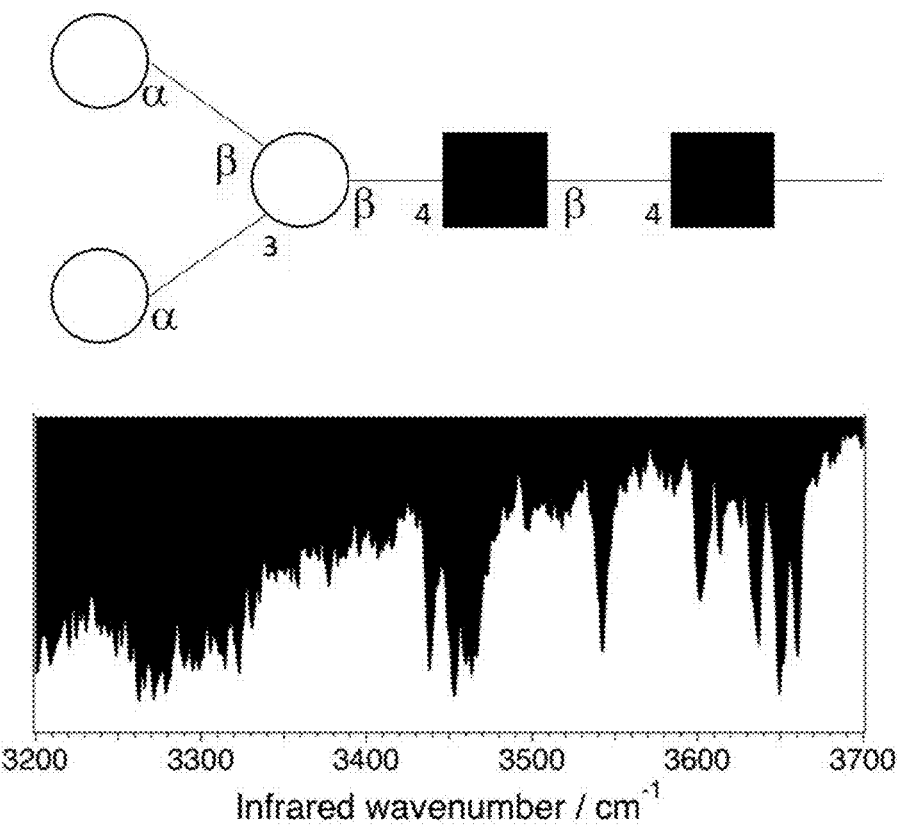
FIG. 14 Cryogenic, vibrational fingerprint spectrum of common core pentasaccharide motif found in all N-glycans.
Figure 15:
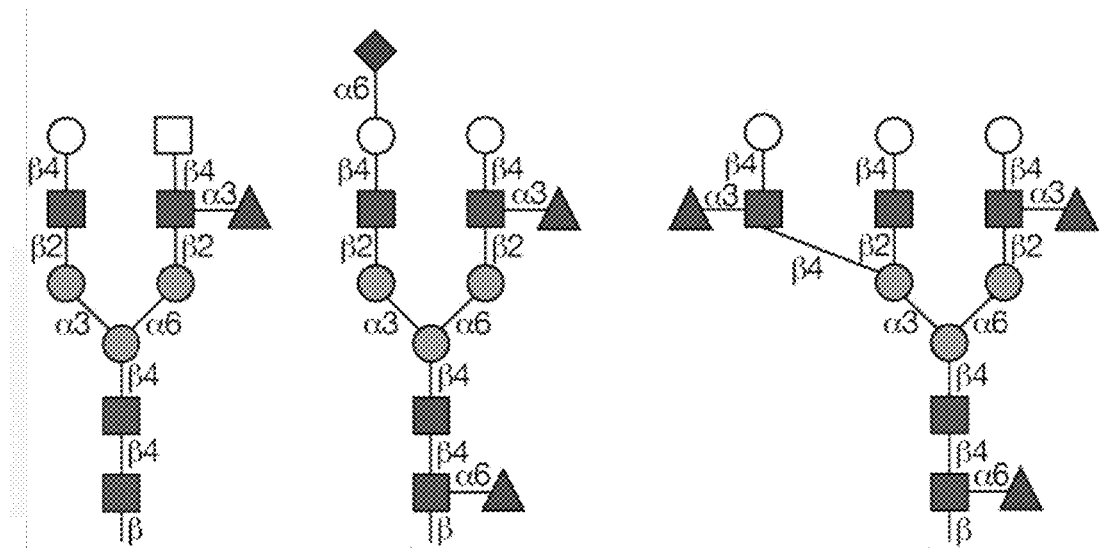
FIG. 15 depicts N-glycans showing the common core structure. Adapted from Ref. [1]

We have already measured the cryogenic vibrational spectrum of this basic core structure, shown in FIG. 14, which exhibits clearly resolved spectral features that constitute distinct pattern by which it can be identified. We will proceed to measure spectra of increasingly complex N-linked glycans, such as those shown in FIG. 15. Each time we add a new species to the database, we gain the ability to quickly recognize it when it appears in a mixture (i.e., using our technique). Thus, by initially focusing on N-linked glycans that are already characterized by other methods, we can quickly construct a database that will be useful for glycan analysis as it progressively expands. Moreover, the high-throughput nature of the experimental approach will expedite expansion of the database.

C. Use of the Database

The application of our experimental technique will result in a multi-dimensional array including values of mass and CCS along with a corresponding vibrational spectrum. For each element of this matrix, we would first search the database for all other species of the same mass, since this is the simplest way to classify glycans. Among those in the database with the same mass, we would then search for those that also match the CCS. For a given mass and CCS, if there is only one match in the database, we would then proceed to compare the measured spectrum with the one tabulated in the database. If this does not match, it signifies that the species we are observing has not yet been added to the database. This case will be discussed in Section D below. If there is more than one entry that has the same mass and CCS, we will then decompose the spectrum into a mixture of the species in the database with the same mass and CCS to obtain their relative concentrations. Because of the multi-dimensional nature of our measurements, we will have already limited the number of possible species that could give rise to the spectrum, and the higher the resolution of our SLIM-based ion mobility separation stage, the fewer this number will be. Nevertheless, even if there are a significant number of isomeric species with overlapping CCS, such as the series of disaccharides shown in FIG. 1, the structured nature of the cryogenic spectra provides a high degree of information content that will make such a decomposition possible.

To help us perform rapid and accurate spectral decompositions to determine the concentrations of glycans in a mixture, data mining and database searching can be employed. Using our proof-of-principle data, they created synthetic spectra of mixtures with added noise and demonstrated that one can rapidly decompose them and obtain accurate relative concentrations. This is because one uses the information content from the entire spectral pattern for identification purposes and not only isolated peaks.

If after attempting a spectral decomposition using the spectra in our database the algorithm does not converge, this is a sign that one or more species with the identified mass and CCS has not been added to the database. We discuss this situation below.

D. The Addition of Unknown Compounds to the Database

While we will initially make a big push to enter as many known glycan structures as possible into our database by running them through our machine and measuring their CCS and vibrational spectrum, as we move to analyzing mixtures of glycans from biological samples, we will certainly encounter species that have not yet been entered in our database, and we need a mechanism by which to determine their primary structure and add them. This will initially be done by combining existing techniques for glycan analysis with our spectroscopic approach. First, we will purify the sample chromatographically, using hydrophilic interaction liquid chromatography (HILIC), for example. We will then follow the usual sequencing procedure and use exoglycosidase digestion to successively cleave off monosaccharides, but in this case we will analyze the resulting products using our spectroscopic technique. If after a particular step in a series of exoglycosidase digests we find that we reduce the unknown species to one that is in our database, then we can stop—together with the particular exoglycosidase(s) that we have used we can determine the structure of the original unknown species as well as the intermediates at each step. As our database grows, starting from the core N-glycan motif shown in FIG. 14, this process will become progressively simpler and faster. Moreover, we only have to go through this time-consuming process once for each unknown species. Once a new compound is added to the database, it can be rapidly identified the basis of its vibrational spectrum whenever it appears in a sample.

Figure 16:
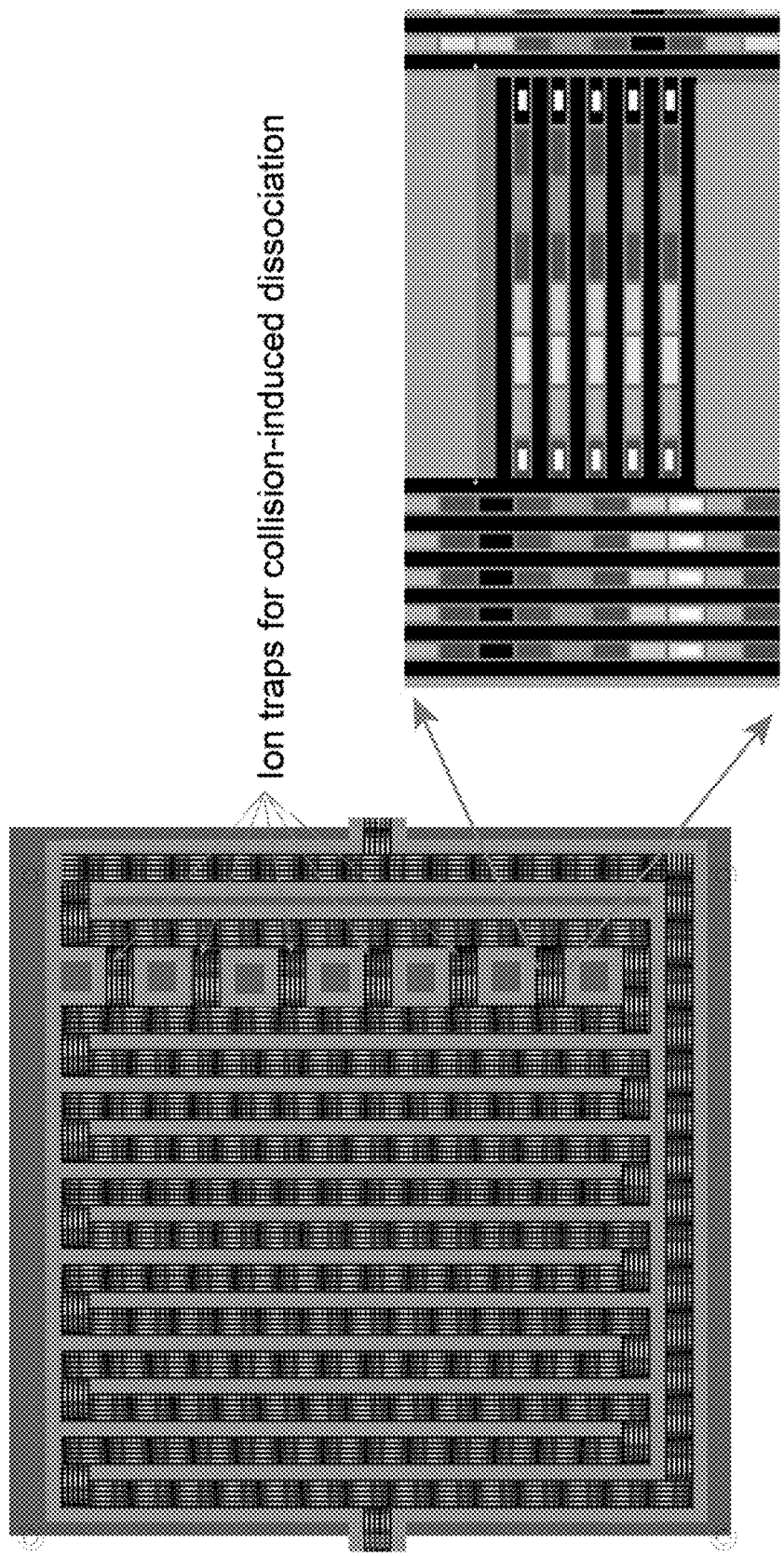
FIG. 16 shows an exemplary SLIM board that incorporates a series of ion traps for collisional dissociation of a parent glycan molecule.

Another method for identifying unknown glycans and adding them to our database is to use our high-throughput approach for measuring vibrational spectra to identify glycan fragments that we generate by breaking up an unknown parent glycan through high-energy collisions. One can then determine the parent structure (although not always uniquely) from the identified fragments. FIG. 16 shows a SLIM board on which we have designed a series of ion traps. We can isolate parent ions in these traps and then fragment them by high energy collisions. We will then analyze the fragments from a particular parent by reinjecting them onto the separation section of the SLIM board, measuring their mobility, using CRIMP to recombine them and then measuring the vibrational spectrum of each of them simultaneously using our cryogenic multi-trap.

CONCLUSIONS

The analysis of glycan structure is undeniably one of the most important challenges to furthering our understanding of the molecular basis of living systems. According to the aspects of the present invention, a high-throughput approach is used in the method and the system to glycan identification will represent a disruptive technology that will enable major breakthroughs in the field of glycoscience. It will provide a powerful new tool for fundamental research in chemical and molecular biology and a practical diagnostic for the pharmaceutical industry. It is the type of novel approach to glycan structure determination called for by the 2012 report of the United States National Academy of Sciences [5].

In sum, according to some aspects of the present invention, a method and system is provided for analyzing glycans with cryogenic vibrational spectroscopy, the method comprising submitting the glycans to an ionizing process to obtain ions; drawing the ions into a vacuum; injecting the ions into an ion mobility section and grouping them in packets, either before or after injection; and in the ion mobility section spatially separating the ions of the packet into subpackets according to their collisional cross section (CCS); and recompressing the subpackets, by removing any empty space between them by means of compression ratio ion mobility programming. The method further comprises loading the ions into a cryogenic ion trap by keeping subpackets with different collisional cross section in respective separate compartments, cooling the ions in collisions with a buffer gas, tagging the ions by attaching one or more messenger molecules and obtaining a weakly bound complex, sending a pulse of infrared light down an axis of the trap to excite vibrations of the cold, trapped, and messenger-tagged ions, and separately ejecting each ion subpacket from the trap into an extraction region of a time-of-flight mass spectrometer and measuring the number of remaining messenger-tagged ions and untagged ions for each subpacket, and this can be done until all the subpackets have been analyzed. A system for performing this method has also been described. A further embodiment of this method is to fragment a parent glycan ion and applying the method to the glycan fragments.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

1. Varki, A., Cummings, R. D., Esko, J. D., Freeze, H. H., Stanley, P., Bertozzi, C. R., Hart, G. W. and Etzler, M. E., *Essentials of Glycobiology* (Cold Spring Harbor Laboratory Press; 2009, Cold Spring Harbor (NY), 2009), 2nd edn.
2. Varki, A.; Biological roles of glycans. Glycobiology. 27, 3-49 (2017).
3. Varki, A.; Biological roles of oligosaccharides: all of the theories are correct. Glycobiology. 3, 97-130 (1993).
4. Dwek, R. A.; Glycobiology: Toward Understanding the Function of Sugars. Chemical Reviews. 96, 683-720 (1996).
5. *Transforming Glycoscience: A Roadmap for the Future* (The National Academies Press, Washington, D.C., 2012).
6. Rudd, P. M., Elliott, T., Cresswell, P., Wilson, I. A. and Dwek, R. A.; Glycosylation and the immune system. Science. 291, 2370-2376 (2001).
7. Karav, S., German, J. B., Rouquie, C., Le Parc, A. and Bartle, D.; Studying Lactoferrin N-Glycosylation. International Journal of Molecular Sciences. 18, 870-870 (2017).
8. Jefferis, R.; Glycosylation as a strategy to improve antibody-based therapeutics. Nature Reviews Drug Discovery. 8, 226-234 (2009).
9. Liu, H. C., Bulseco, G. G. and Sun, J. A.; Effect of posttranslational modifications on the thermal stability of a recombinant monoclonal antibody. Immunology Letters. 106, 144-153 (2006).
10. Mimura, Y., Church, S., Ghirlando, R., Ashton, P. R., Dong, S., Goodall, M., Lund, J. and Jefferis, R.; The influence of glycosylation on the thermal stability and effector function expression of human IgG1-Fc: properties of a series of truncated glycoforms. Molecular Immunology. 37, 697-706 (2000).
11. Sinclair, A. M. and Elliott, S.; Glycoengineering: The effect of glycosylation on the properties of therapeutic proteins. Journal of Pharmaceutical Sciences. 94, 1626-1635 (2005).
12. Jefferis, R.; Recombinant antibody therapeutics: the impact of glycosylation on mechanisms of action. Trends in Pharmacological Sciences. 30, 356-362 (2009).
13. Liu, S., Gao, W. J., Wang, Y., He, Z. Y., Feng, X. J., Liu, B. F. and Liu, X.; Comprehensive N-Glycan Profiling of Cetuximab Biosimilar Candidate by NP-HPLC and MALDI-MS. Plos One. 12, (2017).

14. Ucakturk, E.; Analysis of glycoforms on the glycosylation site and the glycans in monoclonal antibody biopharmaceuticals. J. Sep. Sci. 35, 341-350 (2012).
15. Saldova, R., Kilcoyne, M., Stockmann, H., Martin, S. M., Lewis, A. M., Tuite, C. M. E., Gerlach, J. Q., Le Berre, M., Borys, M. C., Li, Z. J., Abu-Absi, N. R., Leister, K., Joshi, L. and Rudd, P. M.; Advances in analytical methodologies to guide bioprocess engineering for bio-therapeutics. Methods. 116, 63-83 (2017).
16. Laine, R. A.; A calculation of all possible oligosaccharide isomers both branched and linear yields 1.05×10(12) structures for a reducing hexasaccharide—The isomer-barrier to development of single-method saccharide sequencing or synthesis systems. Glycobiology. 4, 759-767 (1994).
17. Marino, K., Bones, J., Kattla, J. J. and Rudd, P. M.; A systematic approach to protein glycosylation analysis: a path through the maze. Nat Chem Biol. 6, 713-723 (2010).
18. Zhang, L., Luo, S. and Zhang, B.; Glycan analysis of therapeutic glycoproteins. mAbs. 8, 205-215 (2016).
19. Gaunitz, S., Nagy, G., Pohl, N. L. B. and Novotny, M. V.; Recent Advances in the Analysis of Complex Glycoproteins. Anal. Chem. 89, 389-413 (2017).
20. Battistel, M. D., Azurmendi, H. F., Yu, B. and Freedberg, D. I.; NMR of glycans: shedding new light on old problems. Progress in nuclear magnetic resonance spectroscopy. 79, 48-68 (2014).
21. Jiménez-Barbero, J., Asensio, J. L., Cañada, F. J. and Poveda, A.; Free and protein-bound carbohydrate structures. Curr. Opin. Chem. Biol. 9, 549-555 (1999).
22. Vliegenthart, J. F., Dorland, L. and van Halbeek, H.; High-resolution, 1H-nuclear magnetic resonance spectroscopy as a tool in the structural analysis of carbohydrates related to glycoproteins. Advances in carbohydrate chemistry and biochemistry. 41, 209-374 (1983).
23. Wormald, M. R., Petrescu, A. J., Pao, Y.-L., Glithero, A., Elliott, T. and Dwek, R. A.; Conformational Studies of Oligosaccharides and Glycopeptides: Complementarity of NMR, X-ray Crystallography, and Molecular Modelling. Chemical Reviews. 102, 371-386 (2002).
24. Aich, U., Lakbub, J. and Liu, A.; State-of-the-art technologies for rapid and high-throughput sample preparation and analysis of N-glycans from antibodies. Electrophoresis. 37, 1468-1488 (2016).
25. Stockmann, H., Duke, R. M., Martin, S. M. and Rudd, P. M.; Ultrahigh Throughput, Ultrafiltration-Based N-Glycomics Platform for Ultraperformance Liquid Chromatography (ULTRA(3)). Anal. Chem. 87, 8316-8322 (2015).
26. Suzuki, S.; Recent Developments in Liquid Chromatography and Capillary Electrophoresis for the Analysis of Glycoprotein Glycans. Analytical Sciences. 29, 1117-1128 (2013).
27. Hemstrom, P. and Irgum, K.; Hydrophilic interaction chromatography. J. Sep. Sci. 29, 1784-1821 (2006).
28. Mittermayr, S., Bones, J. and Guttman, A.; Unraveling the Glyco-Puzzle: Glycan Structure Identification by Capillary Electrophoresis. Anal. Chem. 85, 4228-4238 (2013).
29. Campa, C., Coslovi, A., Flamigni, A. and Rossi, M.; Overview on advances in capillary electrophoresis-mass spectrometry of carbohydrates: a tabulated review. Electrophoresis. 27, 2027-2050 (2006).
30. Mechref, Y. and Novotny, M. V.; Glycomic analysis by capillary electrophoresis-mass spectrometry. Mass Spectrom. Rev. 28, 207-222 (2009).
31. Kailemia, M. J., Li, L. Y., Ly, M., Linhardt, R. J. and Amster, I. J.; Complete Mass Spectral Characterization of a Synthetic Ultralow-Molecular-Weight Heparin Using Collision-Induced Dissociation. Anal. Chem. 84, 5475-5478 (2012).
32. Zaia, J.; Mass spectrometry of oligosaccharides. Mass Spectrom. Rev. 23, 161-227 (2004).
33. Zaia, J.; Mass Spectrometry and Glycomics. Omics-a Journal of Integrative Biology. 14, 401-418 (2010).
34. Yu, X., Jiang, Y., Chen, Y. J., Huang, Y. Q., Costello, C. E. and Lin, C.; Detailed Glycan Structural Characterization by Electronic Excitation Dissociation. Anal. Chem. 85, 10017-10021 (2013).
35. Han, L. and Costello, C. E.; Mass spectrometry of glycans. Biochemistry-Moscow. 78, 710-720 (2013).
36. Kailemia, M. J., Ruhaak, L. R., Lebrilla, C. B. and Amster, I. J.; Oligosaccharide Analysis by Mass Spectrometry: A Review of Recent Developments. Anal. Chem. 86, 196-212 (2014).
37. Gray, C. J., Thomas, B., Upton, R., Migas, L. G., Eyers, C. E., Barran, P. E. and Flitsch, S. L.; Applications of ion mobility mass spectrometry for high throughput, high resolution glycan analysis. Biochim Biophys Acta. 1860, 1688-1709 (2016).
38. Gaye, M. M., Nagy, G., Clemmer, D. E. and Pohl, N. L. B.; Multidimensional Analysis of 16 Glucose Isomers by Ion Mobility Spectrometry. Anal. Chem. 88, 2335-2344 (2016).
39. Hofmann, J., Hahm, H. S., Seeberger, P. H. and Pagel, K.; Identification of carbohydrate anomers using ion mobility-mass spectrometry. Nature. 526, 214-244 (2015).
40. Gaye, M. M., Kurulugama, R. and Clemmer, D. E.; Investigating carbohydrate isomers by IMS-CID-IMS-MS: precursor and fragment ion cross-sections. Analyst. 140, 6922-6932 (2015).
41. Pagel, K. and Harvey, D. J.; Ion Mobility-Mass Spectrometry of Complex Carbohydrates: Collision Cross Sections of Sodiated N-linked Glycans. Anal. Chem. 85, 5138-5145 (2013).
42. Liu, Y. and Clemmer, D. E.; Characterizing oligosaccharides using injected-ion mobility/mass spectrometry. Anal. Chem. 69, 2504-2509 (1997).
43. Lee, S., Wyttenbach, T. and Bowers, M. T.; Gas phase structures of sodiated oligosaccharides by ion mobility/ion chromatography methods. Int. J. Mass Spectrom. 167, 605-614 (1997).
44. Guttman, M. and Lee, K. K.; Site-Specific Mapping of Sialic Acid Linkage Isomers by Ion Mobility Spectrometry. Anal. Chem. 88, 5212-5217 (2016).
45. Royle, L., Radcliffe, C. M., Dwek, R. A. and Rudd, P. M.; Detailed Structural Analysis of N-Glycans Released From Glycoproteins in SDS-PAGE Gel Bands Using HPLC Combined With Exoglycosidase Array Digestions. In: Brockhausen I (ed.). Humana Press, Totowa, N.J., (2007).
46. Zauner, G., Deelder, A. M. and Wuhrer, M.; Recent advances in hydrophilic interaction liquid chromatography (HILIC) for structural glycomics. ELECTROPHORESIS. 32, 3456-3466 (2011).
47. Albrecht, S., Vainauskas, S., Stockmann, H., McManus, C., Taron, C. H. and Rudd, P. M.; Comprehensive Profiling of Glycosphingolipid Glycans Using a Novel Broad Specificity Endoglycoceramidase in a High-Throughput Workflow. Anal. Chem. 88, 4795-4802 (2016).
48. Gotz, L., Abrahams, J. L., Mariethoz, J., Rudd, P. M., Karlsson, N. G., Packer, N. H., Campbell, M. P. and 48. Lisacek, F.; GlycoDigest: a tool for the targeted use of exoglycosidase digestions in glycan structure determination. Bioinformatics. 30, 3131-3133 (2014).
49. Royle, L., Mattu, T. S., Hart, E., Langridge, J. I., Merry, A. H., Murphy, N., Harvey, D. J., Dwek, R. A. and Rudd, P. M.; An analytical and structural database provides a strategy for Sequencing O-glycans from microgram quantities of glycoproteins. Analytical Biochemistry. 304, 70-90 (2002).
50. Shah, B., Jiang, X. G., Chen, L. and Zhang, Z.; LC-MS/MS Peptide Mapping with Automated Data Processing for Routine Profiling of N-Glycans in Immunoglobulins. J. Am. Soc. Mass Spectrom. 25, 999-1011 (2014).
51. Traylor, M. J., Tchoudakova, A. V., Lundquist, A. M., Gill, J. E., Boldog, F. L. and Tangarone, B. S.; Comprehensive Discovery and Quantitation of Protein Heterogeneity via LC-MS/MS Peptide Mapping for Clone Selection of a Therapeutic Protein. Anal. Chem. 88, 9309-9317 (2016).
52. Morelle, W. and Michalski, J.-C.; Analysis of protein glycosylation by mass spectrometry. Nature Protocols. 2, 1585-1602 (2007).
53. Polfer, N. C., Valle, J. J., Moore, D. T., Oomens, J., Eyler, J. R. and Bendiak, B.; Differentiation of isomers by wavelength-tunable infrared multiple-photon dissociation-mass spectrometry: Application to glucose-containing disaccharides. Anal. Chem. 78, 670-679 (2006).
54. Hernandez, O., Isenberg, S., Steinmetz, V., Glish, G. L. and Maitre, P.; Probing Mobility-Selected Saccharide Isomers: Selective Ion-Molecule Reactions and Wavelength-Specific IR Activation. J. Phys. Chem. A. 119, 6057-6064 (2015).
55. Tan, Y. L. and Polfer, N. C.; Linkage and Anomeric Differentiation in Trisaccharides by Sequential Fragmentation and Variable-Wavelength Infrared Photodissociation. J. Am. Soc. Mass Spectrom. 26, 359-368 (2015).
56. Gray, C. J., Schindler, B., Migas, L. G., Pičmanová, M., Allouche, A. R., Green, A. P., Mandal, S., Motawia, M. S., Sánchez-Pérez, R., Bjarnholt, N., Møller, B. L., Rijs, A. M., Barran, P. E., Compagnon, I., Eyers, C. E. and Flitsch, S. L.; Bottom-Up Elucidation of Glycosidic Bond Stereochemistry. Anal. Chem. 89, 4540-4549 (2017).
57. Schindler, B., Barnes, L., Gray, C. J., Chambert, S., Flitsch, S. L., Oomens, J., Daniel, R., Allouche, A. R. and Compagnon, I.; IRMPD Spectroscopy Sheds New (Infrared) Light on the Sulfate Pattern of Carbohydrates. J. Phys. Chem. A. 121, 2114-2120 (2017).
58. Mucha, E., González Flörez, A. I., Marianski, M., Thomas, D. A., Hoffmann, W., Struwe, W. B., Hahm, H. S., Gewinner, S., Schöllkopf, W., Seeberger, P. H., von Helden, G. and Pagel, K.; Glycan Fingerprinting using Cold-Ion Infrared Spectroscopy. Angew. Chem. Int. Ed., n/a-n/a (2017).
59. Masellis, C., Khanal, N., Kamrath, M. Z., Clemmer, D. E. and Rizzo, T. R.; Cryogenic Vibrational Spectroscopy Provides Unique Fingerprints for Glycan Identification. J. Am. Soc. Mass Spectrom. 28, 2217-2222 (2017).
60. Khanal, N., Masellis, C., Kamrath, M. Z., Clemmer, D. E. and Rizzo, T. R.; Glycosaminoglycan analysis by cryogenic messenger-tagging IR spectroscopy combined with IMS-MS. Anal. Chem. 89, 7601-7606 (2017).
61. Hamid, A. M., Ibrahim, Y. M., Garimella, S. V. B., Webb, I. K., Deng, L., Chen, T.-C., Anderson, G. A., Prost, S. A., Norheim, R. V., Tolmachev, A. V. and Smith, R. D.; Characterization of Traveling Wave Ion Mobility Separations in Structures for Lossless Ion Manipulations. Anal. Chem. 87, 11301-11308 (2015).
62. Hebert, D. N., Lamriben, L., Powers, E. T. and Kelly, J. W.; The intrinsic and extrinsic effects of N-linked glycans on glycoproteostasis. Nature Chemical Biology. 10, 902-910 (2014).
63. Hamid, A. M., Garimella, S. V. B., Ibrahim, Y. M., Deng, L., Zheng, X., Webb, I. K., Anderson, G. A., Prost, S. A., Norheim, R. V., Tolmachev, A. V., Baker, E. S. and Smith, R. D.; Achieving High Resolution Ion Mobility Separations Using Traveling Waves in Compact Multiturn Structures for Lossless Ion Manipulations. Anal. Chem. 88, 8949-8956 (2016).
64. Deng, L. L., Ibrahim, Y. M., Baker, E. S., Aly, N. A., Hamid, A. M., Zhang, X., Zheng, X. Y., Garimella, S. V. B., Webb, I. K., Prost, S. A., Sandoval, J. A., Norheim, R. V., Anderson, G. A., Tolmachev, A. V. and Smith, R. D.; Ion Mobility Separations of Isomers based upon Long Path Length Structures for Lossless Ion Manipulations Combined with Mass Spectrometry. Chemistryselect. 1, 2396-2399 (2016).
65. Deng, L., Ibrahim, Y. M., Hamid, A. M., Garimella, S. V. B., Webb, I. K., Zheng, X., Prost, S. A., Sandoval, J. A., Norheim, R. V., Anderson, G. A., Tolmachev, A. V., Baker, E. S. and Smith, R. D.; Ultra-High Resolution Ion Mobility Separations Utilizing Traveling Waves in a 13 m Serpentine Path Length Structures for Lossless Ion Manipulations Module. Anal. Chem. 88, 8957-8964 (2016).
66. Zhang, X., Garimella, S. V. B., Prost, S. A., Webb, I. K., Chen, T.-C., Tang, K., Tolmachev, A. V., Norheim, R. V., Baker, E. S., Anderson, G. A., Ibrahim, Y. M. and Smith, R. D.; Ion Trapping, Storage, and Ejection in Structures for Lossless Ion Manipulations. Anal. Chem. 87, 6010-6016 (2015).
67. Garimella, S. V. B., Ibrahim, Y. M., Webb, I. K., Ipsen, A. B., Chen, T.-C., Tolmachev, A. V., Baker, E. S., Anderson, G. A. and Smith, R. D.; Ion manipulations in structures for lossless ion manipulations (SLIM): computational evaluation of a 90 [degree] turn and a switch. Analyst. 140, 6845-6852 (2015).
68. Webb, I. K., Garimella, S. V. B., Tolmachev, A. V., Chen, T.-C., Zhang, X., Norheim, R. V., Prost, S. A., LaMarche, B., Anderson, G. A., Ibrahim, Y. M. and Smith, R. D.; Experimental Evaluation and Optimization of Structures for Lossless Ion Manipulations for Ion Mobility Spectrometry with Time-of-Flight Mass Spectrometry. Anal. Chem. 86, 9169-9176 (2014).
69. Garimella, S. V. B., Hamid, A. M., Deng, L., Ibrahim, Y. M., Webb, I. K., Baker, E. S., Prost, S. A., Norheim, R. V., Anderson, G. A. and Smith, R. D.; Squeezing of Ion Populations and Peaks in Traveling Wave Ion Mobility Separations and Structures for Lossless Ion Manipulations Using Compression Ratio Ion Mobility Programming. Anal. Chem. 88, 11877-11885 (2016).
70. Masson, A., Kamrath, M. Z., Perez, M. A. S., Glover, M. S., Rothlisberger, U., Clemmer, D. E. and Rizzo, T. R.; Infrared Spectroscopy of Mobility-Selected H+-Gly-Pro-Gly-Gly (GPGG). J. Am. Soc. Mass Spectrom. 26, 1444-1454 (2015).
71. Goebbert, D. J., Wende, T., Bergmann, R., Meijer, G. and Asmis, K. R.; Messenger-Tagging Electrosprayed Ions: Vibrational Spectroscopy of Suberate Dianions. J. Phys. Chem. A. 113, 5874-5880 (2009).
72. Aseev, O., Perez, M. A. S., Rothlisberger, U. and Rizzo, T. R.; Cryogenic Spectroscopy and Quantum Molecular Dynamics Determine the Structure of Cyclic Intermediates Involved in Peptide Sequence Scrambling. J. Chem. Phys. Lett. 6, 2524-2529 (2015).

73. Nagornova, N. S., Guglielmi, M., Doemer, M., Tavernelli, I., Rothlisberger, U., Rizzo, T. R. and Boyarkin, O. V.; Cold-Ion Spectroscopy Reveals the Intrinsic Structure of a Decapeptide. Angew. Chem. Int. Ed. 50, 5383-5386 (2011).
74. Campbell, M. P., Ranzinger, R., Lutteke, T., Mariethoz, J., Hayes, C. A., Zhang, J. Y., Akune, Y., Aoki-Kinoshita, K. F., Damerell, D., Carta, G., York, W. S., Haslam, S. M., Narimatsu, H., Rudd, P. M., Karlsson, N. G., Packer, N. H. and Lisacek, F.; Toolboxes for a standardised and systematic study of glycans. Bmc Bioinformatics. 15, (2014).
75. Lisacek, F., Mariethoz, J., Alocci, D., Rudd, P. M., Abrahams, J. L., Campbell, M. P., Packer, N. H., Stahle, J., Widmalm, G., Mullen, E., Adamczyk, B., Rojas-Macias, M. A., Jin, C. and Karlsson, N. G.; Databases and Associated Tools for Glycomics and Glycoproteomics. Methods in molecular biology (Clifton, N. J.). 1503, 235-264 (2017).
76. Walsh, I., Zhao, S., Campbell, M., Taron, C. H. and Rudd, P. M.; Quantitative profiling of glycans and glycopeptides: an informatics' perspective. Curr. Opin. Chem. Biol. 40, 70-80 (2016).
77. Campbell, M. P., Royle, L., Radcliffe, C. M., Dwek, R. A. and Rudd, P. M.; GlycoBase and autoGU: tools for HPLC-based glycan analysis. Bioinformatics. 24, 1214-1216 (2008).
78. Hayes, C. A., Karlsson, N. G., Struwe, W. B., Lisacek, F., Rudd, P. M., Packer, N. H. and Campbell, M. P.; UniCarb-DB: a database resource for glycomic discovery. Bioinformatics. 27, 1343-1344 (2011).
79. Glaskin, R. S., Khatri, K., Wang, Q., Zaia, J. and Costello, C. E.; Construction of a Database of Collision Cross Section Values for Glycopeptides, Glycans, and Peptides Determined by IM-MS. Anal. Chem. 89, 4452-4460 (2017).
80. Struwe, W. B., Pagel, K., Benesch, J. L. P., Harvey, D. J. and Campbell, M. P.; GlycoMob: an ion mobility-mass spectrometry collision cross section database for glycomics. Glycoconjugate Journal. 33, 399-404 (2016).
81. Kornfeld, R. and Kornfeld, S.; Assembly of asparagine-linked oligosaccharides. Annual Review of Biochemistry. 54, 631-664 (1985).

The invention claimed is:

1. A method for analyzing a plurality of molecules with cryogenic vibrational spectroscopy, the method comprising:
    providing a packet of molecules in a ionized form;
    injecting the packet into an ion mobility section;
    spatially separating the ions of the packet into subpackets according to their collisional cross section (CCS);
    recompressing the subpackets, by removing an empty space between them;
    loading the ions into a cryogenic ion trap by keeping subpackets with different CSS in a respective separate compartment;
    cooling the ions in collisions with a buffer gas;
    tagging the ions by attaching a messenger molecule;
    sending a pulse of infrared light down an axis of the trap to excite vibrations of the cold, trapped, and messenger-tagged ions; and
    separately ejecting ion subpacket from the trap into an extraction region of a time-of-flight mass spectrometer and measuring the number of remaining messenger-tagged ions and untagged ions for each subpacket.

2. The method of claim 1, wherein the step of separately ejecting is performed until all the subpackets have been analyzed.
3. The method of claim 1, further comprising:
    repeating the sequence of measurements for different wavelengths of the infrared light pulse; and
    generating an infrared spectrum for each subpacket of ions including the fraction of tagged ions as a function of the infrared wavelength.
4. The method of claim 1, further comprising:
    measuring an ion drift time, a mass, and an infrared spectrum for each ion subpacket; and
    comparing the data obtained from the measurements to entries of a determined database to identify species of the molecules.
5. The method of claim 1, wherein providing a packet of molecules in a ionized form comprises:
    submitting the plurality of molecules to an ionising process to obtain ions; and
    grouping the ions into a packet.
6. The method of claim 1, wherein the infrared light pulse is generated by an optical parametric oscillator.
7. The method of claim 1, wherein the infrared light pulse is generated by fiber laser pumped solid state laser.
8. The method of claim 1, wherein the buffer gas is $N_2$.
9. The method of claim 1, a messenger molecule of the messenger-tagged ions is $N_2$.
10. The method of claim 1, wherein the ion mobility section is a SLIM device.
11. The method of claim 1, further comprising:
    isolating one subpacket of molecules in the ion mobility section; and
    fragmenting the sub packet while still in the ion mobility section, thereby obtaining subpackets including the ion fragments of the initially isolated molecules.
12. The method of claim 1, wherein the molecules are selected from a list comprising glycans, polypeptides, nucleic acids, lipids, primary metabolites, and secondary metabolites.
13. A system for analyzing a plurality of molecules with cryogenic vibrational spectroscopy, the system comprising:
    a structure for lossless ion manipulations (SLIM) including an ion mobility section for receiving a packet of molecules in a ionized form, the SLIM configured for spatially separating the ions of the packet into subpackets according to a collisional cross section (CCS) of the ions, for keeping subpackets with different CCS in a respective separate compartment, and for recompressing the subpackets by removing an empty space between them;
    a cryogenic ion trap for cooling the ions in collision with a buffer gas and for tagging the ions by attaching a messenger molecule;
    an optical light source providing an infrared light to the cryogenic ion trap to excite vibrations of the cold, trapped, and messenger-tagged ions; and
    a time-of-flight mass spectrometer having an extraction region for separately receiving ion subpackets from the cryogenic ion trap for measuring the number of remaining messenger-tagged ions and untagged ions for each subpacket.
14. The system of claim 13, wherein the optical light source includes an optical parametric oscillator (OPO) for generating the infrared light.

* * * * *